(12) United States Patent
Lu et al.

(10) Patent No.: US 11,400,410 B2
(45) Date of Patent: Aug. 2, 2022

(54) COMPOSITIONS AND METHODS FOR CARBON DIOXIDE CAPTURE

(71) Applicant: The Board of Trustees of the University of Illinois, Urbana, IL (US)

(72) Inventors: Yongqi Lu, Urbana, IL (US); Yang Du, Champaign, IL (US); Qing Ye, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 438 days.

(21) Appl. No.: 16/374,471

(22) Filed: Apr. 3, 2019

(65) Prior Publication Data

US 2019/0329176 A1     Oct. 31, 2019

Related U.S. Application Data

(60) Provisional application No. 62/814,146, filed on Mar. 5, 2019, provisional application No. 62/663,483, filed on Apr. 27, 2018.

(51) Int. Cl.
  *B01D 53/14*     (2006.01)
  *B01D 53/62*     (2006.01)
  (Continued)

(52) U.S. Cl.
  CPC ..... *B01D 53/1493* (2013.01); *B01D 53/1425* (2013.01); *B01D 53/1475* (2013.01);
  (Continued)

(58) Field of Classification Search
  None
  See application file for complete search history.

(56) References Cited

U.S. PATENT DOCUMENTS 7,541,011 B2    6/2009   Hu
7,846,407 B2   12/2010   Hu
(Continued)

FOREIGN PATENT DOCUMENTS

CN    103657382 A    3/2014
CN    105709566 B    8/2018
(Continued)

OTHER PUBLICATIONS

"Safety Data Sheet for 1,1,3,3-Tetramethylguanidine." TCI America (2014). Viewed online at https://www.chemblink.com/MSDS/MSDSFiles/80-70-6_TCI.pdf on Oct. 5, 2021.*
(Continued)

*Primary Examiner* — Daniel Berns
(74) *Attorney, Agent, or Firm* — Haukaas Fortius PLLC; Michael H. Haukaas

(57) ABSTRACT

An aqueous solvent composition is provided, comprising a nucleophilic component having one or more sterically unhindered primary or secondary amine moieties, a Brønsted base component having one or more basic nitrogen moieties, a water-soluble organic solvent, and water. A biphasic composition is provided, comprising one or more carbamate compounds, one or more conjugate acids of Brønsted base, a water-soluble organic solvent, and water. A biphasic $CO_2$ absorption process is also provided, utilizing the biphasic solvent composition.

17 Claims, 14 Drawing Sheets

Before $CO_2$ absorption: A homogeneous phase

During $CO_2$ absorption: A and B absorb $CO_2$ via a "shuttle" mechanism; dual phases formed After $CO_2$ absorption: $CO_2$ enriched in aqueous phase; phase separation evolved

(51) Int. Cl.
| | |
|---|---|
| *B01D 53/78* | (2006.01) |
| *B01D 53/96* | (2006.01) |
| *C07C 211/03* | (2006.01) |
| *C07C 211/06* | (2006.01) |
| *C07C 211/11* | (2006.01) |
| *C07C 211/13* | (2006.01) |
| *C07C 211/17* | (2006.01) |
| *C07D 213/16* | (2006.01) |
| *C07D 265/30* | (2006.01) |
| *C07D 221/00* | (2006.01) |
| *C07D 241/04* | (2006.01) |
| *C07D 223/04* | (2006.01) |
| *C07D 235/00* | (2006.01) |

(52) U.S. Cl.
CPC .............. *B01D 53/62* (2013.01); *B01D 53/78* (2013.01); *B01D 53/96* (2013.01); *C07C 211/03* (2013.01); *C07C 211/06* (2013.01); *C07C 211/11* (2013.01); *C07C 211/13* (2013.01); *C07C 211/17* (2013.01); *C07D 213/16* (2013.01); *C07D 221/00* (2013.01); *C07D 223/04* (2013.01); *C07D 235/00* (2013.01); *C07D 241/04* (2013.01); *C07D 265/30* (2013.01); *B01D 2252/2041* (2013.01); *B01D 2252/20405* (2013.01); *B01D 2252/20415* (2013.01); *B01D 2252/20421* (2013.01); *B01D 2252/20426* (2013.01); *B01D 2252/20431* (2013.01); *B01D 2252/20442* (2013.01); *B01D 2252/20447* (2013.01); *B01D 2252/20473* (2013.01); *B01D 2252/20484* (2013.01); *B01D 2252/504* (2013.01); *B01D 2257/504* (2013.01); *B01D 2258/0283* (2013.01)

(56) References Cited

U.S. PATENT DOCUMENTS

| | | | | |
|---|---|---|---|---|
| 8,715,397 | B2* | 5/2014 | Kortunov | B01D 53/62 95/199 |
| 2008/0078292 | A1 | 4/2008 | Mimura et al. | |
| 2012/0061614 | A1* | 3/2012 | Calabro | B01D 53/1475 252/184 |
| 2017/0216763 | A1 | 8/2017 | Widger et al. | |

FOREIGN PATENT DOCUMENTS

| | | |
|---|---|---|
| WO | 2009027491 A1 | 3/2009 |
| WO | 2013000953 A2 | 1/2013 |

OTHER PUBLICATIONS

"Piperazine Anhydrous for Synthesis MSDS." Loba Chemie (2015). Viewed online at https://www.lobachemie.com/lab-chemical-msds/MSDS-PIPERAZINE-ANHYDROUS-CASNO-110-85-05285-EN.aspx on Oct. 5, 2021.*
"Material Safety Data Sheet for Dimethyl Sulfoxide." ScienceLab.com (2013). Viewed online at https://www.vanderbilt.edu/vinse/facilities/safety_data_sheets/Dimethyl_sulfoxide_DMSO.pdf on Oct. 5, 2021.*
Astarita et al., "Promotion of CO2 Mass Transfer in Carbonate Solutions," Chem Eng Sci., 37(3):581-588, Dec. 1982.
Bruder et al., "Solvent Comparison for Postcombustion CO2 Capture," 1st Post Combustion Capture Conference, May 2011; 3pgs.
Davis J.D., "Thermal Degradation of Aqueous Amines Used for Carbon Dioxide Capture," Thesis, The University of Texas at Austin, Aug. 2009, 307pgs.
Eide-Haugmo et al., "A Study of Thermal Degradation of Different Amines and Their Resulting Degradation Products," 1st Post Combustion Capture Conference, May 17-19, 2011, 2pgs.
Ghosh et al., "Organic Carbamates in Drug Design and Medicinal Chemistry," J Med Chem., 58(7):2895-2940, Apr. 2015.
Huang, Q., "Thermal Degradation of Amines for CO2 Capture," Thesis, University of Kentucky, 2015, 126pgs.
Kim et al., "Carbon Dioxide Absorption Using a Phase Transitional Alkanolamine-Alcohol Mixture," J End Eng Chem., 20(4):1486-1492, Jul. 2014.
Lee et al., "Phase Separation Characteristics in Biphasic Solvents Based on Mutually Miscible Amines for Energy Efficient CO2 Capture," Korean J Chem Eng., 34(6):1840-1845, Apr. 2017.
Monteiro et al., "Kinetics of CO2 Absorption in Aqueous Blends of N,N-diethylethanolamine (DEEA) and N-methyl-1,3-propanediamine (MAPA)," Chem Eng Sci., 129:145-155, Jun. 2015.
Rochelle et al., "Degradation of Amines in CO2 Capture," Luminant Carbon Management Program, The University of Texas at Austin, Presented at TCCS-6, Jun. 2011.
Xu et al., "CO2 Absorption by Biphasic Solvents: Mixtures of 1,4-Butanediamine and 2-(Diethylamino)-ethanol," Int J Greenh Gas Con., 16:107-115, Aug. 2013.
Xu et al., "Study on Potential Biphasic Solvents: Absorption Capacity, CO2 Loading and Reaction Rate," Energy Procedia, 37:494-498, Dec. 2013.
Ye et al., "Experimental Investigation and Thermodynamic Modeling of Phase Transition and Equilibria in a Biphasic Solvent System for CO2 Capture," Ind Eng Chem Res., 57(29):9627-9640, Jun. 2018.
Zhang et al., "Development of an Rnergy-efficient CO2 Capture Process Using Thermomorphic Biphasic Solvents," Energy Procedia, 37:1254-1261, Dec. 2013.
Zhang et al., "Novel Thermomorphic Biphasic Amine Solvents for CO2 Absorption and Low-Temperature Extractive Regeneration," Chem Eng Technol., 34(9):1481-1489, Sep. 2011.
Zheng et al., "Capturing CO2 into the Precipitate of a Phase-Changing Solvent after Absorption," Environ Sci Technol., 48(15):8905-8910, Jun. 2014.
Rochelle, G., "Thermal Degradation of Amines for CO2 Capture," Curr Opin Chem Eng., 1(2):183-190, May 2012.

\* cited by examiner t = ~480 min, ~23% desorption at 80°C: dual phases remained and CO₂ rich in the lower phase (4.85 mol/L, ~70 vol%) and lean in the other (0.21 mol/L)

t = ~240 min, ~18% desorption at 80°C: dual phases formed and CO₂ rich in the lower phase (5.23 mol/L, ~70 vol%) and lean in the other (0.17 mol/L)

t = 0 min, before CO₂ desorption: CO₂-rich phase (4.52 mol/L) obtained from CO₂-loaded solvent; one single phase (homogeneous)

Fig. 12

COMPOSITIONS AND METHODS FOR CARBON DIOXIDE CAPTURE

RELATED APPLICATIONS

This application claims priority under 35 U.S.C. § 119(e) to U.S. Provisional Patent Application No. 62/663,483 filed Apr. 27, 2018 and U.S. Provisional Patent Application No. 62/814,146 filed Mar. 5, 2019, which applications are incorporated herein by reference.

GOVERNMENT SUPPORT

This invention was made with government support under DE-FE0004360 and DE-FE0026434 awarded by the United States Department of Energy. The government has certain rights in the invention.

BACKGROUND OF THE INVENTION

Current state-of-the-art post-combustion carbon capture (PCC) technologies are energy intensive and expensive. According to the United States Department of Energy/National Energy Technology Laboratory (USDOE/NETL) study entitled "Cost and Performance Baseline for Fossil Energy Plants," the benchmark monoethanolamine (MEA) process for $CO_2$ capture will consume nearly 30% of the electricity output in a coal-fired power plant. A 550-MWe supercritical pulverized coal-fired power plant equipped with the MEA process will increase the cost of electricity (COE; 2007$) from $59/MWh without $CO_2$ capture to $107/MWh with $CO_2$ capture, equivalent to an approximately 80% increase in COE or $48/tonne of $CO_2$ captured (or $69/tonne $CO_2$ avoided). Among the $CO_2$ capture cost, the majority is attributable to parasitic power loss (60%), followed by capital costs (30%) and then non-energy related operation and maintenance (O&M) costs (10%). Such levels of energy use and cost are projected to be prohibitive for deployment of carbon capture in the markets. Therefore, a significant cut in cost and energy use is required before PCC becomes a practical option for carbon reduction. For example, the USDOE's cost goal is targeted at a 35% COE increase at 90% carbon removal.

A conventional $CO_2$ capture process employs a monophasic solvent to absorb $CO_2$ from a gas stream in an absorber and then desorb the absorbed $CO_2$ and regenerate the solvent in a stripper at an elevated temperature in a closed absorption-desorption loop to achieve gas separation. A possible alternative to the conventional single-phase amine scrubbing process is using a new type of biphasic solvents that can undergo a liquid-liquid phase separation after the loading of $CO_2$ with the absorbed $CO_2$ enriched in one liquid phase and lean in the other. Because only the $CO_2$-rich liquid phase needs be regenerated, the mass of the solvent required for thermal regeneration, and thus the related energy use and equipment footprint (i.e., capital cost), can be significantly reduced compared with the conventional $CO_2$ capture processes.

Despite these desirable characteristics, the application of biphasic solvents in the industry may be limited by their high viscosity, especially that of the $CO_2$-rich liquid phase, and the high volatility of some solvent components. The high solvent viscosity causes low heat transfer and mass transfer rates, making prohibitive the costs of the cross-heat exchanger, absorber column, and stripping column used in the process. The high solvent volatility causes excess solvent loss and environmental issues. The present disclosure provides compositions and methods of solvent formulation to alleviate the high viscosity and high volatility concerns associated with biphasic solvents without a concurrent reduction in their $CO_2$ capture performance.

The viscosity of $CO_2$-rich liquid phase is related to the extent of phasic separation. A high degree of phase separation (i.e., $CO_2$ concentrated in a small volume of a phase) will reduce the mass of the solvent for regeneration, but also result in high viscosity. In conventional biphasic solvents reported in the literature, the extent of phasic separation can only be regulated by changing the concentrations of amine components. However, the change of amine concentration can significantly affect the $CO_2$ capture performance. As such, improved biphasic solvents are needed.

Accordingly, there is a need for an improved energy efficient means of capturing carbon dioxide. Therefore, capturing a higher loading of carbon dioxide in a fluid of minimal viscosity is needed for lowering energy expenditure.

SUMMARY

This disclosure provides various homogeneous aqueous compositions comprising amines and organic solvents for capturing carbon dioxide.

Accordingly, this disclosure provides an aqueous composition comprising:
a) at least one nucleophilic compound, wherein the nucleophilic compound comprises a sterically unhindered primary amine moiety, a sterically unhindered secondary amine moiety, or a combination thereof,
b) at least one Brønsted base, wherein the Brønsted base comprises a basic nitrogen moiety and the Brønsted base does not comprise either a sterically unhindered primary amine moiety or a sterically unhindered secondary amine moiety;
c) about 5% to about 50% by weight of a water-soluble organic solvent; and
d) about 5% to about 40% by weight of water;
wherein the combination of the nucleophilic compound, the Brønsted base, the organic solvent, and the water components of the composition are at least 80% miscible within a temperature range of 20° C. to 80° C.

This disclosure also provides a biphasic composition comprising:
a) a carbamate compound comprising a carbamate moiety of at least one of a primary amine and a secondary amine;
b) a Brønsted base wherein the Brønsted base is in the form of its conjugate acid, wherein the Brønsted base does not form a carbamate moiety with carbon dioxide;
c) about 5% to about 50% by weight of a water-soluble organic solvent; and
d) about 5% to about 40% by weight of water;
wherein the biphasic composition has a $CO_2$-rich phase and a $CO_2$-lean phase;
wherein the rich phase comprises the highest % weight of water, the highest % weight of the carbamate compound, and the highest % weight of the conjugate acid; and the lean phase comprises the highest % weight of the organic solvent.

Additionally, this disclosure provides a method for capturing carbon dioxide comprising contacting carbon dioxide gas with an aqueous composition according to the above disclosed aqueous composition;

wherein
  a) the nucleophilic compound and carbon dioxide gas form a carbamate moiety via the nitrogen atom of the primary or secondary amine moiety to provide a carbamate compound;
  b) the Brønsted base forms a conjugate acid wherein the dissolution of carbon dioxide gas is facilitated;
  c) the water in the aqueous composition becomes enriched with the carbamate compound; and
  d) the aqueous composition partitions to form a biphasic composition that has a $CO_2$-rich phase and a $CO_2$-lean phase, wherein the rich phase comprises the highest % weight of water, the highest % weight of the carbamate compound, and the highest % weight of the conjugate acid; and the lean phase comprises the highest % weight of the organic solvent;
wherein carbon dioxide is thereby captured.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 12. Photographs taken before cleaning by glass bead blasting for carbon steel C1010 (CS-C1010) coupons in MEA and the biphasic solvents BiS4 and BiS6 under different corrosion test conditions.

DETAILED DESCRIPTION

Figure 1:
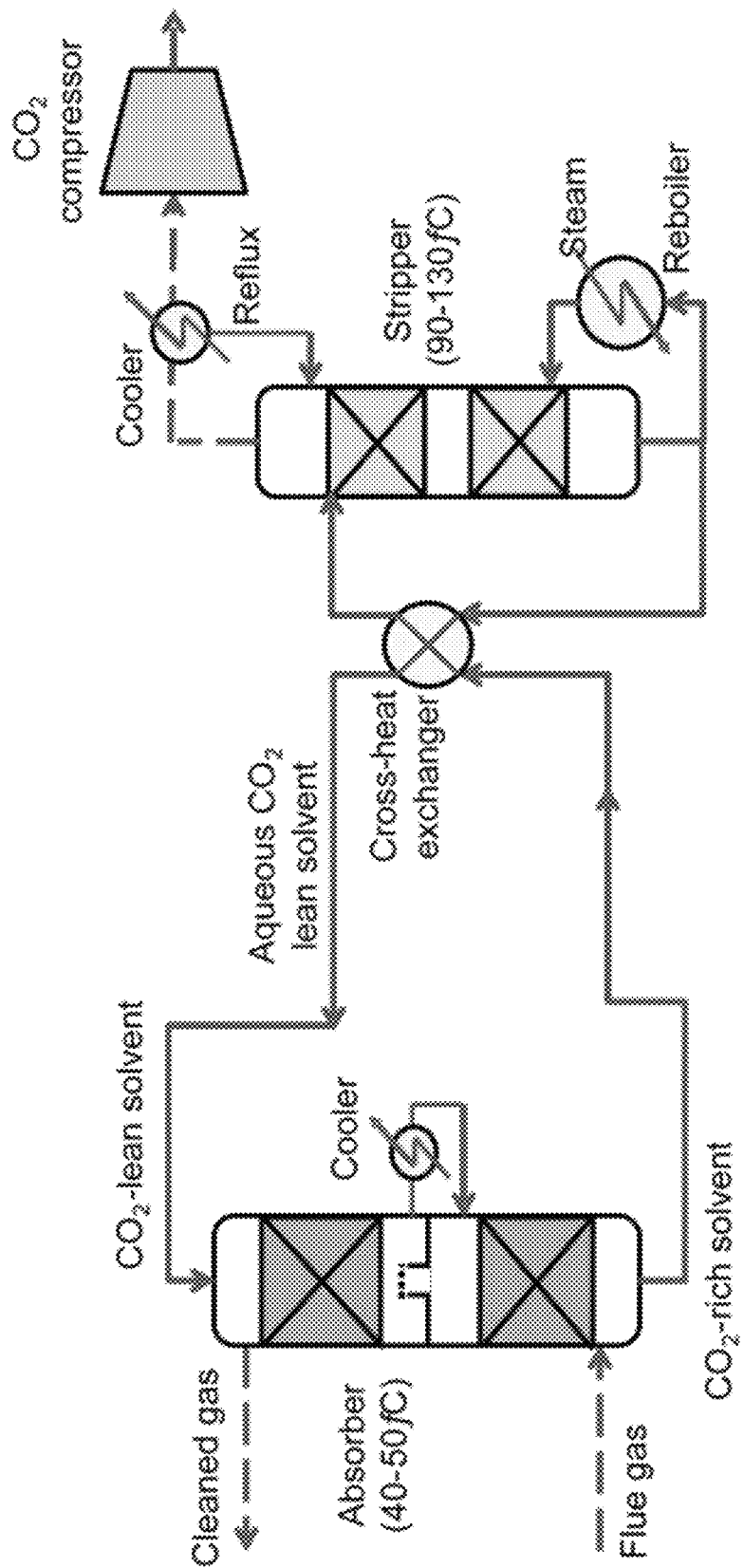
FIG. 1. Schematic diagram of conventional monophasic $CO_2$ absorption processes for PCC.

The compositions and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the molecular level, for example, to bring about a chemical reaction, or a physical change, e.g., in a solution, in a reaction mixture.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

The term "amine" as used herein is an alkylamine or a nitrogen heterocycle. The alkylamine can be a primary, secondary or tertiary amine. For example, a primary amine has one alkyl substituent, a secondary amine has two alkyl substituents, and a tertiary amine has three alkyl substituents. A nitrogen heterocycle has at least one nitrogen atom and the heterocycle can be non-aromatic or aromatic (e.g., an aromatic compound having a ring of conjugated pi-electrons). A nitrogen heterocycle that is non-aromatic can be, for example, a cyclic amine wherein the amine moiety is a secondary or tertiary amine.

Certain amine compounds, such as a secondary amine, can be hindered or non-hindered. A person of ordinary skill in the art can distinguish between hindered and non-hindered amines by visual inspection of an amine compound's two- or three-dimensional structure, and/or the amine compound's reactivity with other chemical species. For example, an unhindered alkylamine compound is a compound wherein its electron pair on the amine nitrogen atom is not sterically hindered or encumbered by substituents on the alkylamine, and wherein the electron pair can react with an electrophile to form a new bond that is "stable" (e.g. does not spontaneously break at temperatures within 0° C. to 100° C.). In further examples, carbon dioxide could react with a sterically unhindered primary amine compound to form a "secondary" carbamate moiety, or react with a sterically unhindered secondary amine compound to form a "tertiary" carbamate moiety. In another example, a sterically hindered secondary amine could have one or more substituents at the carbon atom that is directly bonded to the nitrogen atom (e.g., the alpha-positions). Such sterically hindered secondary amines would not readily or substantially react with electrophiles such as carbon dioxide because the nitrogen electron pair is sterically blocked from approaching an electrophile close enough to form a covalent bond. Similarly, a sterically hindered primary amine compound could have the electron pair of the nitrogen atom buried and/or blocked by the molecule's substituents, thereby rendering it unreactive or less reactive compared to the reactivity of a sterically unhindered primary amine. Tertiary amines (and aromatic nitrogen heterocycles) described in this disclosure are unreactive to (or poorly reactive with) carbon dioxide. For example, bond formation of the tertiary amine with carbon dioxide is at most transient in nature (i.e., unstable, reversible, or having a short half-life—e.g., $t_{1/2}$<10 minutes).

The term "nucleophilic compound" as used herein is a chemical species, such as an amine, that donates an electron pair to an electrophile, such as carbon dioxide, to form a chemical bond in relation to a reaction. For example, a primary amine's free pair of electrons would react with carbon dioxide to form a carbamate compound having a carbamate group or moiety.

The term "Brønsted base" means a compound which is a proton acceptor. As used herein, the Brønsted base is a tertiary alkylamine (acyclic or cyclic) or an aromatic nitrogen heterocycle that forms its conjugate acid by exchange of a proton (the hydrogen cation, or H+), and does not form a covalent bond to carbon dioxide, as discussed above. A primary or secondary amine that is sufficiently sterically encumbered could satisfy the conditions required of the Brønsted base for the purposes of this disclosure.

Embodiments of the Invention

The disclosure herein provides an aqueous composition comprising:
 a) at least one nucleophilic compound, wherein the nucleophilic compound comprises a sterically unhindered primary amine moiety, a sterically unhindered secondary amine moiety, or a combination thereof;
 b) at least one Brønsted base, wherein the Brønsted base comprises a basic nitrogen moiety and the Brønsted base does not comprise either a sterically unhindered primary amine moiety or a sterically unhindered secondary amine moiety;
 c) about 5% to about 50% by weight of a water-soluble organic solvent; and
 d) about 5% to about 40% by weight of water;
wherein the combination of the nucleophilic compound, the Brønsted base, the organic solvent, and the water components of the composition are at least 80% miscible within a temperature range of 20° C. to 80° C.

A Brønsted base can be at least one Brønsted base or two or more different Brønsted bases. Similarly, a nucleophilic compound can be at least one nucleophilic compound or two or more different nucleophilic compounds, and a carbamate compound can be at least one carbamate compound or two or more different carbamate compounds.

Percent miscibility can be determined by measuring the amounts of each separated liquid phase that forms (or the particulates that separate from a liquid phase) wherein the separated phases (or particulates) can each be measured by volume or weight.

In various additional embodiments, the percent weight of the water-soluble organic solvent is about 1% to about 90%, about 2% to about 75%, about 3% to about 60%, about 4% to about 45%, about 6% to about 40%, about 7% to about 35%, about 8% to about 25%, or about 10% to about 40%. In various other embodiments, the percent weight of water is about 1% to about 85%, about 2% to about 75%, about 3% to about 60%, about 4% to about 45%, about 6% to about 40%, about 7% to about 35%, about 8% to about 25%, or about 10% to about 40%.

In some embodiments, the organic solvent can be a combination of one or more organic solvents that are partially to fully soluble in water. In other embodiments, the components of the composition can be partially to fully miscible. For example, one or more components of the composition can be 100% miscible to 1% miscible in the composition. In other embodiments, 100% miscibility of the components of the composition would provide a fully (100%) homogeneous mixture; and in other embodiments, less than 100% miscibility would provide a mixture that is less than 100% homogeneous. In other embodiments, miscibility of the components in the composition is about 10%, about 20%, about 30%, about 40%, about 50%, about 60%, about 70%, about 75%, or about 90%.

In some various embodiments, the composition is a homogeneous mixture within the temperature range of 20° C. to 80° C. In other embodiments, the combination of the nucleophilic compound, the Brønsted base, the organic solvent, and the water components of the composition are completely miscible within the temperature range of 20° C. to 80° C. In further embodiments, the boiling points of the nucleophilic compound, Brønsted base, and organic solvent are each at least 140° C. In yet other embodiments, the vapor pressures of the nucleophilic compound, Brønsted base, and organic solvent are each about 100 Pa or below at about 20° C. The boiling points and vapor pressures recited refer to each of the individual components in a purified form, but in other embodiments, these recited numerical values for said properties are for each of the components that form the composition.

In additional embodiments, the temperature range is within 0° C. to 150° C., or within 25° C. to 100° C. In some other embodiments, homogeneity of the components in the composition is about 10%, about 20%, about 30%, about 40%, about 50%, about 60%, about 70%, about 80%, about 90%, or about 100%. In yet other embodiments, the boiling points of the nucleophilic compound, Brønsted base, and organic solvent are about 80° C. to about 200° C. In further embodiments, the vapor pressures of the nucleophilic compound, Brønsted base, and organic solvent are about 20 Pa to about 250 Pa at about 20° C., or about 1 Pa to about 80 Pa at about 20° C.

In some additional embodiments, the composition comprises about 10% to about 40% by weight of the nucleophilic compound, and about 10% to about 60% by weight of the Brønsted base. In yet some further embodiments, the composition comprises about 10% to about 60% by weight of the Brønsted base. In other embodiments, the composition comprises about 10% to about 40% by weight of the nucleophilic compound. In some embodiments, the nucleophilic compound does not comprise a tertiary amine moiety.

In other embodiments, the percent weight of the nucleophilic compound is about 5%, about 15%, about 25%, about 35%, about 45%, about 55%, about 65%, about 75%, or about 85%. In yet other embodiments, the percent weight of the Brønsted base is about 5%, about 15%, about 25%, about 35%, about 45%, about 55%, about 65%, about 75%, or about 85%.

In further embodiments, the Brønsted base comprises (or essentially consists of) a nitrogen heterocycle, a tertiary amine moiety, or a sterically hindered secondary amine moiety wherein the sterically hindered secondary amine moiety does not form a carbamate moiety with carbon dioxide (the sterically hindered amines could form an unstable carbamate moiety that spontaneously reverses to the base and $CO_2$ at temperatures above 0° C., above 25° C., above 50° C., above 100° C., or 0° C. to 150° C.). In some other embodiments, the Brønsted base does not comprise one of or both a secondary amine and primary amine. In yet other embodiments, the Brønsted base comprises only tertiary amines or only an aromatic nitrogen heterocycle.

In other embodiments, the nucleophilic compound or the Brønsted base has a total of 1-6 nitrogen atoms. In other embodiments, the pKa of at least one nitrogen atom of the Brønsted base is about 7 to about 15. In some other embodiments, the total number of nitrogen atoms in the nucleophilic compound or the Brønsted base is 1-5, 1-4, or 1-3. In yet other embodiments, the pKa of at least one nitrogen atom of the Brønsted base is about 8, about 9, about 10, about 11, about 12, about 13, or about 14.

In additional embodiments, the Brønsted base comprises an imidazole, a piperazine, a morpholine, a piperidine, a guanidine, an amino ether, a non-alcoholic tertiary amine, a non-alcoholic sterically hindered amine, or a combination thereof; and the molecular weight of the Brønsted base is about 60 daltons to about 250 daltons, about 70 daltons to about 225 daltons, about 75 daltons to about 220 daltons, or about 65 daltons to about 230 daltons.

In other embodiments, the Brønsted base is 2-ethylimidazole, 2-ethyl-4-methylimidazole, 1,4-bis(2-hydroxyethyl) piperazine, 4-(2-hydroxyethyl)morpholine, 4-hydroxy-1-methylpiperidine, 1,1,3,3-tetramethylguanidine, bis[2-(N,N-dimethylamino)ethyl] ether, N,N,N',N'',N''-pentamethyldiethylenetriamine, N,N,N',N'',N''-pentamethyldipropylenetriamine, triethylenediamine, 3,3'-iminobis(N,N-dimethylpropylamine), di-sec-butylamine, N-propyl-sec-butylamine, 2-amino-2-methyl-1-propanol, 2-(isopropylamino)ethanol, 2-[2-(dimethylamino)ethoxy] ethanol, or a combination thereof.

In further embodiments, the nucleophilic compound comprises a piperidine, an imidazole, a piperazine, a morpholine, an amino ether, a non-alcoholic polyamine, a non-alcoholic monoamine, or a combination thereof; and the molecular weight of the nucleophilic compound is about 60 daltons to about 250 daltons, about 70 daltons to about 225 daltons, about 75 daltons to about 220 daltons, or about 65 daltons to about 230 daltons.

In yet some other embodiments, the nucleophilic compound is piperazine, 2-methyl-piperazine, 1-(2-hydroxyethyl)piperazine, 1-(2-aminoethyl)piperazine, 4-(2-aminoethyl)morpholine, bis(2-aminoethyl) ether, bis(3-aminopropyl)amine, 1,3-diaminopropane, 3,3'-diamino-N-methyldipropylamine, 3-(aminomethyl)pyridine, 1-(3-aminopropyl)imidazole, hexamethyleneimine, N-methylcyclohexylamine, 2-piperidineethanol, or a combination thereof.

In additional embodiments, the nucleophilic compound comprises at least two secondary amine moieties. In other embodiments, the nucleophilic compound comprises a secondary amine moiety that is a ring-member of a heterocycle. In some further embodiments, the organic solvent comprises an ether, ester, acetal, aldehyde, ketone, glyme, lactam, sulfolane, urea, or a combination thereof. In yet other embodiments, the organic solvent has a pKa no greater than 7 and is inert to carbon dioxide. An organic solvent that is inert to carbon dioxide means that it does not react with carbon dioxide. The inert organic solvent might react with carbon dioxide only under forcing conditions such as with the use of a catalyst, for example at temperatures above 160° C.

In further embodiments, the viscosity of the composition is 10 cP or less at 20° C. In other embodiments, the viscosity of the composition is 20 cP or less at 20° C., or about 1 cP to about 15 cP at 20° C.

In other embodiments, the organic solvent comprises N-methyl-2-pyrrolidone, 1,3-dimethyl-2-imidazolidinone, triethylene glycol dimethyl ether (triglyme), tetraethylene glycol dimethyl ether (tetraglyme), or a combination thereof.

This disclosure also provides a biphasic composition comprising:
  a) a carbamate compound comprising a carbamate moiety of at least one of a primary and a secondary amine;
  wherein optionally the carbamate compound does not comprise a tertiary amine moiety;
  b) a Brønsted base wherein the Brønsted base is in the form of its conjugate acid, wherein the Brønsted base does not form a carbamate moiety with carbon dioxide;
  wherein the Brønsted base does not comprise a primary amine moiety and a secondary amine moiety that can form a carbamate moiety with carbon dioxide (however, the Brønsted base could form an unstable carbamate moiety that spontaneously reverses to the base and $CO_2$ at temperatures above 0° C.);
  c) about 5% to about 50% by weight of a water-soluble organic solvent; and
  d) about 5% to about 40% by weight of water;
  wherein the biphasic composition has a $CO_2$-rich phase and a $CO_2$-lean phase;
  wherein the rich phase comprises the highest % weight of water, the highest % weight of the carbamate compound, and the highest % weight of the conjugate acid; and the lean phase comprises the highest % weight of the organic solvent.

In some embodiments, the carbamate compound comprises a primary carbamate moiety, a secondary carbamate moiety, or both a primary carbamate moiety and a secondary carbamate moiety.

In some various embodiments, the $CO_2$-rich phase is a top layer that is less dense than the $CO_2$-lean phase and therefore the top layer floats above the $CO_2$-lean phase which is the bottom layer. In some other embodiments, the $CO_2$-lean phase is a top layer that is less dense than the $CO_2$-rich phase and therefore the top layer floats above the $CO_2$-rich phase which is the bottom layer.

In other additional embodiments, the organic solvent comprises glyme. In further embodiments, the composition comprises up to about 3 mole equivalents (or about 0.5 mole equivalents to about 3 mole equivalents) of carbamate moieties (or the total amount of captured carbon dioxide in the composition is about 0.1 mole to about 3 moles including organic carbamates and inorganic carbonates and bicarbonates per liter of biphasic composition) per liter of the biphasic composition. In additional embodiments, the mole equivalents of carbamate moieties comprised by each liter of biphasic composition is about 0.5, about 1, about 1.5, about 2, or about 2.5 mole equivalents. In some additional embodiments, the number of moles of the total amount of carbon dioxide (i.e., organic carbamates and inorganic carbonates and bicarbonates) comprised by each liter biphasic composition is about 0.5, about 1, about 1.5, about 2, or about 2.5 moles.

In further embodiments, the $CO_2$-rich phase comprises up to about 6.5 mole equivalents (or about 0.5 mole equivalents to about 6.5 mole equivalents) of carbamate moieties (or the total amount of captured carbon dioxide in the $CO_2$-rich phase is about 1 mole to about 6.5 moles including organic carbamates and inorganic carbonates and bicarbonates per liter of the $CO_2$-rich phase) per liter of the $CO_2$-rich phase. In some further embodiments, the mole equivalents of carbamate moieties comprised by each liter of the $CO_2$-rich phase is about 0.5, about 1, about 1.5, about 2, about 2.5, about 3, about 3.5, about 4, about 4.5, about 5, about 5.5 mole, or about 6 mole equivalents. In some other embodiments, the number of moles of the total amount of carbon dioxide (i.e., organic carbamates and inorganic carbonates and bicarbonates) comprised by each liter of the $CO_2$-rich phase is about 0.5, about 1, about 1.5, about 2, about 2.5, about 3, about 3.5, about 4, about 4.5, about 5, about 5.5 moles, or about 6 moles.

In yet other embodiments, the organic solvent comprises glyme, the composition comprises about 0.5 mole equivalents to about 3 mole equivalents of carbamate moieties per liter of the biphasic composition, the $CO_2$-rich phase comprises about 0.5 mole equivalents to about 6.5 mole equivalents of carbamate moieties per liter of the $CO_2$-rich phase, or a combination thereof.

The term "mole equivalents", for example for carbamate moieties, refers to the mole equivalents of captured carbon dioxide (e.g., one mole of a carbamate compound could have 2 or more mole equivalents of captured carbon dioxide if the carbamate moieties were formed from a compound having two or more sterically unhindered primary or secondary amines).

In further embodiments, the composition is in contact with a gas comprising about 96% by volume oxygen and about 4% by volume carbon dioxide, and one or more metal catalysts;
wherein the composition oxidatively degrades at a loss-rate of less than 10% by weight in 10 days at 50° C. (compared with a loss rate of 41% for 30% by weight of monoethanolamine (MEA) at the same conditions).

In further embodiments, when the $CO_2$-rich phase is, for example, sealed in a stainless-steel tube and heated in an oven, the $CO_2$-rich phase when heated is thermally degraded at a loss-rate of less than about 12% by weight in 14 days at 150° C.

In some other embodiments, the metal catalyst comprises $FeSO_4$, $MnSO_4$, $NiSO_4$ (e.g., a 10 ppm to 20,000 ppm standard solution), a 1,000 ppm $Cr^{3+}$ ion standard solution, or a combination thereof. In other embodiments, the metal catalyst is added to the composition to accelerate the decomposition.

In other embodiments, the organic solvent comprises tetraglyme, the Brønsted base is 2-ethyl-4-methylimidazole, and the nucleophilic compound is piperazine, 2-methylpiperazine, or a combination thereof. In some embodiments, the composition is 2-4-fold less corrosive to carbon steel than a 30% by weight MEA aqueous solution when the composition and MEA are under absorption conditions at about 40° C. or desorption conditions at 120° C. to 150° C.

Additionally, this disclosure provides a method for capturing carbon dioxide comprising contacting carbon dioxide gas with an aqueous composition herein disclosed;
wherein
a) the nucleophilic compound and carbon dioxide gas form a carbamate moiety via the nitrogen atom of the primary or secondary amine moiety to provide a carbamate compound;
b) the Brønsted base forms a conjugate acid wherein the dissolution of carbon dioxide gas is facilitated;
c) the water in the aqueous composition becomes enriched with the carbamate compound; and d) the aqueous composition partitions to form a biphasic composition that has a $CO_2$-rich phase and a $CO_2$-lean phase, wherein the rich phase comprises the highest % weight of water, the highest % weight of the carbamate compound, and the highest % weight of the conjugate acid; and the lean phase comprises the highest % weight of the organic solvent;
wherein carbon dioxide is thereby captured.

In various embodiments, the organic solvent comprises tetraglyme, the Brønsted base is 2-ethyl-4-methylimidazole, and the nucleophilic compound is piperazine, 2-methylpiperazine, or a combination thereof.

In other embodiments, the method further comprising heating the $CO_2$-rich phase at about 100° C. to about 160° C. to release captured carbon dioxide as molecular carbon dioxide; and (optionally) recovering recycled nucleophilic compounds and Brønsted bases. In some embodiments, the amount of energy used to release molecular carbon dioxide at 100° C. to 160° C. is less compared to the release of molecular carbon dioxide from a monophasic composition comprising 30% by weight of MEA at 100° C. to 125° C.

In some other embodiments the $CO_2$-rich phase is heated at about 80° C. to about 180° C., about 110° C. to about 170° C., about 120° C. to about 150° C., or about 125° C. to about 145° C.

Additionally, this disclosure provides a method of processing carbon dioxide comprising:
a) contacting carbon dioxide gas and the aqueous composition according to the compositions disclosed herein in one or more absorption columns to form a biphasic composition comprising a carbamate compound, a $CO_2$-rich phase, and a $CO_2$-lean phase;
b) at least partially separating the $CO_2$-rich phase from the $CO_2$-lean phase in one or more liquid-liquid phase separation (LLPS) units, wherein the at least partially separated $CO_2$-rich phase is dispatched from the one or more LLPS units;
c) feeding the $CO_2$-rich phase to one or more thermal strippers and heating the $CO_2$-rich phase to a temperature that releases an amine compound and molecular carbon dioxide from the carbamate compound;
wherein
i) the $CO_2$-rich phase is optionally preheated, wherein the preheated $CO_2$-rich phase is fed to the middle or lower portion of the one or more thermal strippers; or
ii) the $CO_2$-rich phase is not preheated, wherein the not preheated $CO_2$-rich phase is fed to the top portion of the one or more thermal strippers;
d) returning the amine compound to the one or more absorption columns; and
e) compressing the molecular carbon dioxide with one or more compressors into liquid carbon dioxide;
wherein carbon dioxide is thereby processed from a gas to a liquid.

In various other embodiments, the one or more thermal strippers comprise a second LLPS unit, a second $CO_2$-lean phase is at least partially separated from a second $CO_2$-rich phase in the second LLPS unit, and the at least partially separated second $CO_2$-lean phase is dispatched from the second LLPS unit.

In some embodiments, the liquid carbon dioxide is a supercritical fluid.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2, 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion

The present disclosure provides a $CO_2$ absorption technology enabled by a new class of biphasic solvents comprising three main components (abbreviated as A, B, and C) in addition to a small amount of water (mostly <40 wt %). Component A is used as an absorption accelerator, which is chosen from compounds with one or more primary (—$NH_2$) or secondary (—NH) amino groups. Component B enhances the $CO_2$ loading capacity and serves as a phase separation promoter, which is a compound with one or more tertiary or sterically hindered amino groups or one or more other basic nitrogen groups. Component C is a low-viscosity, water-soluble organic solvent to regulate the LLPS behavior of the solvent blend. Water is used to maintain the solvent blend at a relatively low viscosity with increasing $CO_2$ uptake.

Figure 3:
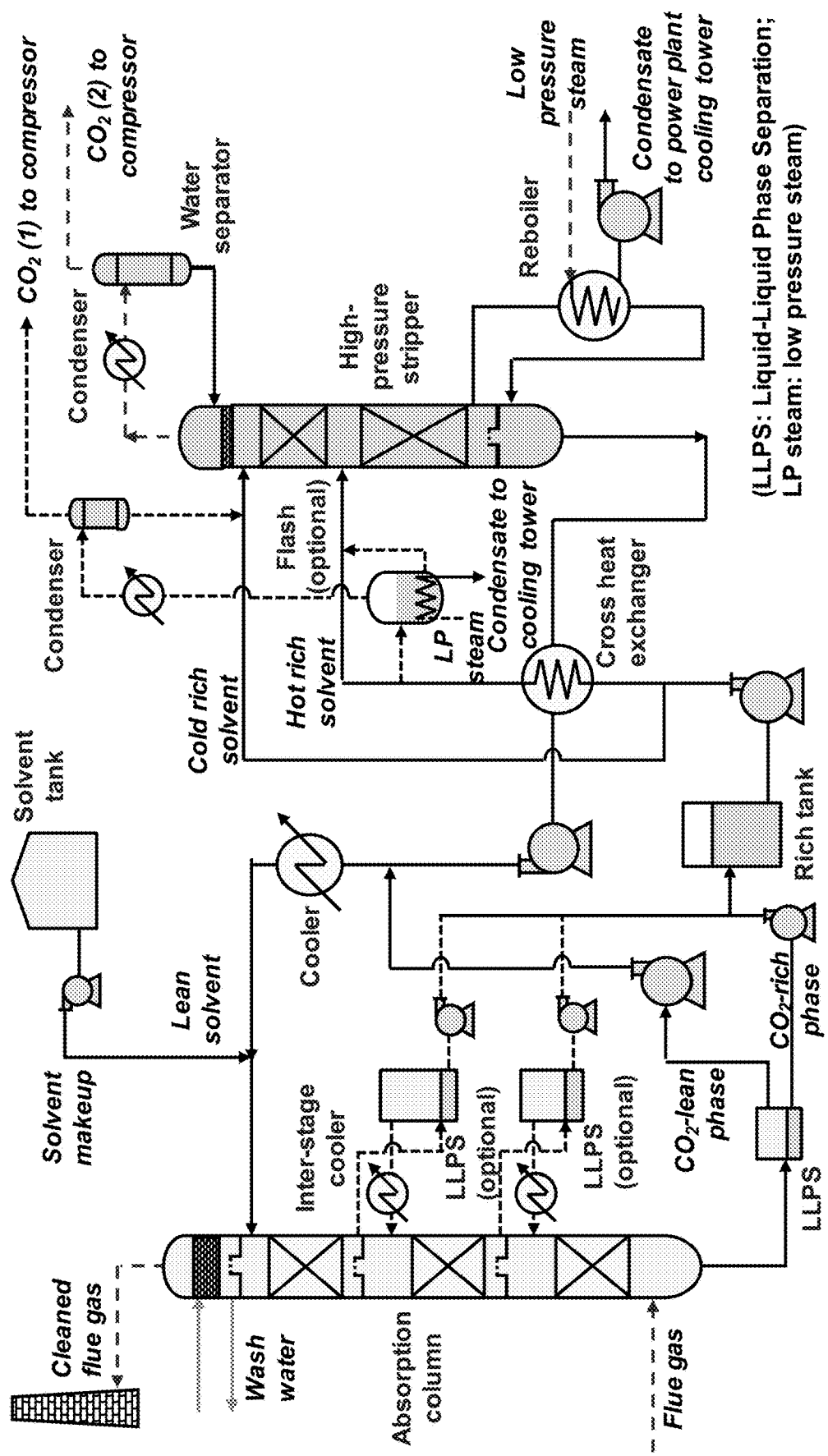
FIG. 3. Schematic diagram of the biphasic $CO_2$ absorption process (optional with multiple stages of liquid-liquid phase separation [LLPS]). Three stages of LLPS are shown in this illustration.

Enabled by this new class of biphasic solvents, a novel biphasic $CO_2$ absorption process (abbreviated hereafter as BiCAP) has been developed. A schematic diagram of the BiCAP is shown in FIG. 3. After a $SO_2$ polishing treatment, flue gas enters the absorber, where the $CO_2$ is absorbed into a biphasic solvent at about 30° C. to about 50° C. and atmospheric pressure. The absorption column has multiple stages (typically two to three sections of packing), and between any two adjacent stages, the option exists to attach an LLPS tank.

Compared with the conventional monophasic solvent-based absorption processes, the absorbed $CO_2$ is highly concentrated in the rich phase as a result of the phase separation and the mass of the rich solvent that requires thermal regeneration in the proposed technology decreases significantly. The reduced mass of solvent with a high $CO_2$ loading for regeneration reduces both the sensible heat and stripping heat requirements and the size of the cross-heat exchanger and the stripper.

Compared with the other reported biphasic solvent-based process concepts, the invented technology also has the following unique features:

The disclosed biphasic solvents feature the introduction of a low-volatility, low-viscosity, water-soluble organic compound to regulate the extent of phasic separation. The viscosity of $CO_2$-rich liquid phase is related to the extent of phasic separation. A high degree of phase separation (i.e., a low volumetric ratio of the $CO_2$-rich to the $CO_2$-lean phase) will reduce the mass of the solvent for regeneration but will also result in high viscosity. In conventional biphasic solvents, the extent of phasic separation can only be regulated by changing the amine concentration. However, the change of amine concentration can significantly affect the $CO_2$ absorption performance. The new biphasic solvents disclosed herein, the extent of phasic separation is regulated by changing the concentration of the organic compound, which does not affect the $CO_2$ absorption performance.

The co-presence of water and a less polar organic compound creates two different levels of medium affinity to the molecular and ionic species, which have different degrees of hydrophilicity, thus effectively facilitating the occurrence and development of dual liquid phases during $CO_2$ absorption. With this unique approach, a large number of solvent blends can be formulated to form dual liquid phase systems. This would largely increase the potential for identifying biphasic solvents with the desired properties for PCC. By comparison, only a limited number of choices of aqueous amine-based biphasic solvents have been reported.

Biphasic Solvents:

The new class of biphasic solvents are composed of three main components A, B, and C in addition to a small amount of water (e.g. <40 wt %) to ensure a desirable absorption rate and $CO_2$ capacity while facilitating a required phase separation and $CO_2$ enrichment.

Component A, a compound having one or more primary or secondary amino groups is a rate promoter and capacity contributor, is an organic compound having one or more primary or secondary amino groups and in some embodiments is selected from piperazines, pyridine, morpholines and their derivatives, amino ethers, non-alcoholic polyamines, non-alcoholic monoamines (linear, cyclic or heterocyclic, saturated or unsaturated, aliphatic or aromatic), imidazoles, amides, imides, or a combination thereof. More specifically, Component A is selected from 3-(aminomethyl) pyridine, 1,3-diaminopropane, 2-piperidineethanol, piperazine, 2-methyl-piperazine, 1-(2-hydroxyethyl)piperazine, 1-(2-aminoethyl)piperazine, 4-(2-aminoethyl)morpholine, bis(3-aminopropyl)amine, hexylamine, hexamethyleneimine, N-methylcyclohexylamine, bis(2-aminoethyl) ether, 3,3'-diamino-N-methyldipropylamine, or 1-(3-aminopropyl) imidazole. Component A can also be a combination of two or more chemicals listed above.

Component B, having one or more tertiary or sterically hindered amino groups or other basic nitrogen groups, is a capacity enhancer, and is an organic compound selected from imidazoles, piperazines, pyridines, morpholines, piperidines, guanidines, amides, imides, amino ethers, non-alcoholic tertiary amines, non-alcoholic sterically hindered amines, or a combination thereof. Some embodiments may contain at least one tertiary amino group. More specifically, Component B is selected from 2-[2-(dimethylamino)ethoxy] ethanol, triethylenediamine, 3-quinuclidinol, 4-(2-hydroxyethyl)morpholine, 4-hydroxy-1-methylpiperidine, bis[2-(N,N-dimethylamino)ethyl] ether, N,N,N',N'',N''-pentamethyldiethylenetriamine, N,N,N',N'',N''-pentamethyldipropylenetriamine, 2-ethylimidazole, 2-ethyl-4-methylimidazole, di-sec-butylamine, N-propyl-sec-butylamine, 1,1,3,3-tetramethylguanidine, 1,4-bis(2-hydroxyethyl)piperazine, or 3,3'-iminobis(N,N-dimethylpropylamine). Component B can be a combination of two or more chemicals listed above.

Component C is an inert water-soluble organic solvent selected from ethers, esters, ketones, acetals, aldehydes, glymes, lactams, sulfolane, urea, or a combination thereof. More specifically, Component C can be either N-methyl-2-pyrrolidone, 1,3-dimethyl-2-imidazolidinone, triethylene glycol dimethyl ether (triglyme), tetraethylene glycol dimethyl ether (tetraglyme), or a combination thereof.

The above formulated biphasic solvents contain the total concentration of the compound having one or more primary or secondary amino groups (Component A) and the compound having one or more tertiary or sterically hindered amino groups or other basic nitrogen groups (Component B) ranging from about 20 wt % to about 70 wt % and the concentration of organic solvent (Component C) is from about 5 wt % to about 50 wt %.

Figure 4:
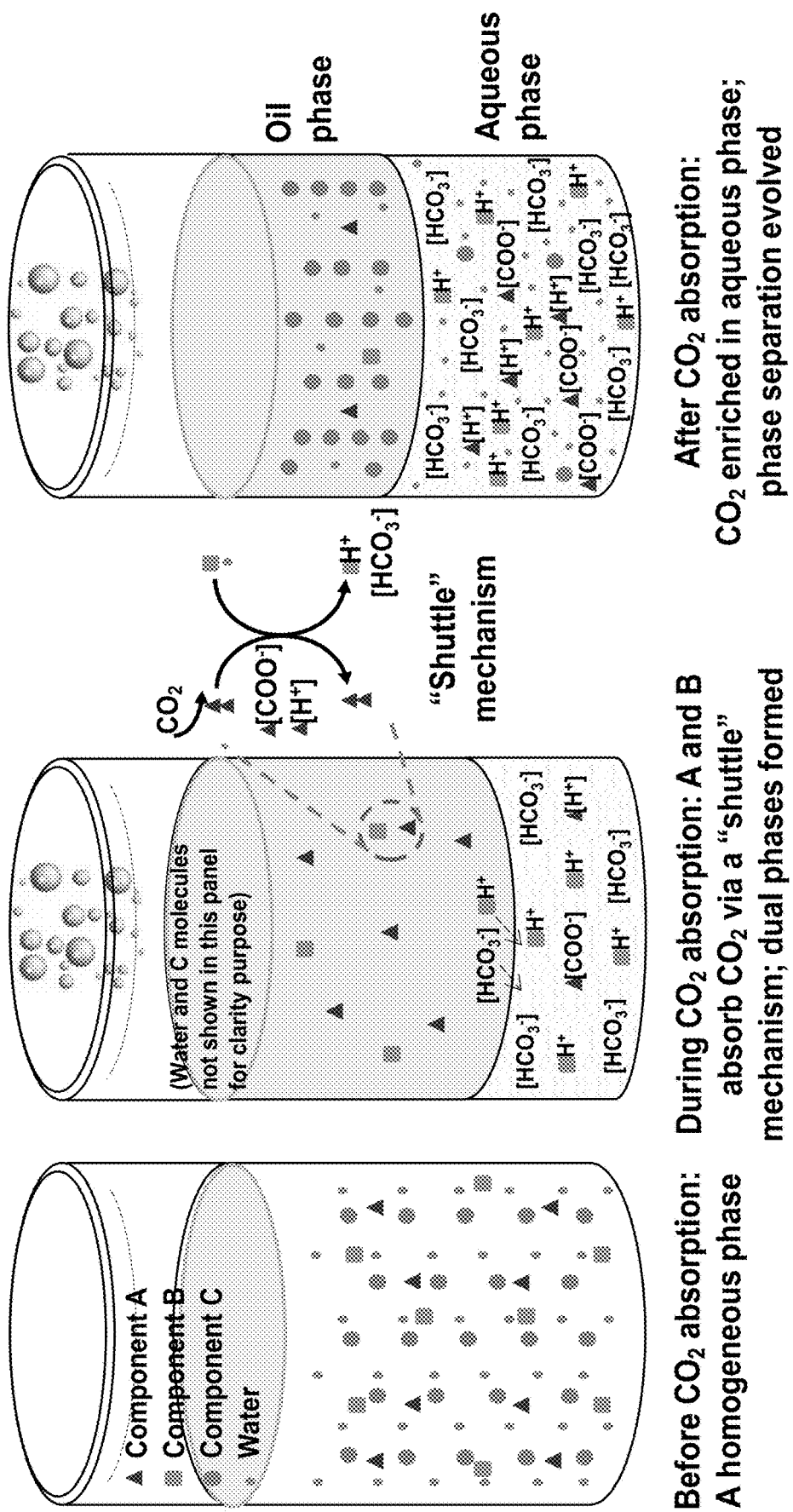
FIG. 4. Conceptual mechanism of $CO_2$ absorption and LLPS in the invented biphasic solvent.

The chemistry and mechanism of $CO_2$ absorption and LLPS in the biphasic solvent are illustrated in FIG. 4. The mutual solubility of two liquids depends on their polarities. In amine-based solvents, the mutual solubility of organic Component C and water can be affected by the absorption reactions and the formation of ionic species, thus incurring a phase separation. In the biphasic solvent system, the ionic products of $CO_2$ reactions prevail in the aqueous phase ($CO_2$ rich; more water present than organic C while unreacted compounds partition in the oily phase ($CO_2$ lean; more organic C than water). The combination of Components A and B follows the "shuttle mechanism" for enhancing the performance of $CO_2$ absorption.

The BiCAP solvents based on the invented approach can be formulated with numerous choices of solvent components and precise control of the phase separation behavior enabled by the use of a unique low-viscosity, water-soluble organic solubilizer (Component C). The identified biphasic solvents revealed high stability, low volatility, low viscosity, and commercial availability in large quantities in addition to their superior $CO_2$ capture performance.

A unique absorption process configuration incorporating multiple stages of LLPS allows separation and removal of the $CO_2$-rich liquid phase (more viscous than the $CO_2$-lean liquid phase) during $CO_2$ absorption, thus maintaining rapid kinetics and minimizing the concern of high solvent viscosity.

The BiCAP uses a stripper configuration that features a portion of rich phase solvent as a cold stream (with no or little pre-heating via heat exchange) to the top of the stripper and the other as a hot stream after heat exchange to the middle part of the stripper. Such a unique configuration for biphasic solvents further reduces the stripping heat.

The BiCAP allows a unique incorporation of LLPS in $CO_2$ desorption. The LLPS operates to separate and remove the $CO_2$-lean phase from the $CO_2$-rich phase formed during the $CO_2$ desorption. As a result, $CO_2$ loading can remain at high levels over the course of $CO_2$ desorption, thus allowing the desorption operating at a high pressure. In addition, because a portion of the regenerated solvent is removed via LLPS, the size of the desorber may be reduced.

Method of $CO_2$ Capture:

The absorption step can be a multistage combination of absorption and LLPS configuration. At each stage, the $CO_2$-rich liquid phase can be partially or completely separated and removed from the absorber. As a result, the solvent is able to maintain low viscosity and thus retain a rapid mass transfer rate throughout the $CO_2$ absorption process. This configuration thus allows the use of a solvent with a relatively high concentration or high viscosity.

The desorption step features a stripper configuration with a portion of the $CO_2$-rich phase solvent directly fed to the top of the stripper without heat exchange (i.e., cold rich solvent stream). Thus, the temperature at the stripper top is lowered, resulting in a reduced concentration of water vapor in the product $CO_2$ stream (i.e., reduced use of stripping heat). The other portion of the rich phase solvent is preheated in a cross-heat exchanger (i.e., hot rich solvent stream) before feeding into the middle of the stripper. The location of the hot rich solvent feed may be optimized and selected to minimize both the stripping heat usage and packing height requirement. Because of the reduced mass of rich solvent required for heat exchange, the size of the cross-heat exchanger is reduced.

Based on the above unique features, this invention can significantly reduce both the energy use and equipment cost for $CO_2$ separation and compression compared with not only the benchmark MEA process but also the common biphasic solvent-based processes reported by others.

The purpose of the present disclosure is to provide a transformational, low cost solution for PCC. The technology is developed in an attempt to take advantage of a new type of biphasic solvent materials and a unique phase separation operation to significantly improve energy efficiency and thus reduce the associated parasitic power loss and the related O&M cost. Meanwhile, the technology can also incur small footprint and reduce the capital cost.

The disclosed biphasic solvents feature the introduction of a low-volatility, low-viscosity, water-soluble organic compound to regulate the extent of phase separation and control the viscosity. As the extent of phase separation is regulated by changing the concentration of the organic solvent compound (Component C), it does not affect the $CO_2$ absorption performance.

The co-presence of water and the organic solvent compound (Component C) also effectively facilitates the occurrence and development of dual liquid phases during $CO_2$ absorption. With this unique approach, a large number of solvent blends can be formulated to form dual liquid phase systems. This largely increases the potential for identifying biphasic solvents with the desired properties, such as large $CO_2$ capacity, fast kinetics, low viscosity, low volatility, and high stability.

In addition, the absorption step can be a multistage combination of absorption and LLPS configuration. At each stage, the $CO_2$-rich liquid phase can be partially or completely separated and removed from the absorber. As a result, the solvent is able to maintain low viscosity and thus retain a rapid mass transfer rate throughout the $CO_2$ absorption process. This configuration thus allows the use of a solvent with a relatively high concentration or high viscosity. The desorption step features a stripper configuration with a portion of the $CO_2$-rich phase solvent directly fed to the top of the stripper without heat exchange. Thus, the temperature at the stripper top is lowered, resulting in a reduced amount of water vapor in the product $CO_2$ stream (e.g. reduced use of stripping heat associated with water evaporation). The other portion of the rich phase solvent is preheated in a cross-heat exchanger before flowing into the optimal location of the stripper. Because of the reduced mass of rich solvent required for heat exchange, the size of the cross-heat exchanger is reduced.

A schematic diagram of the conventional monophasic $CO_2$ absorption processes is illustrated in FIG. 1. The system consists of an absorber and a desorber. In the absorber, $CO_2$ is separated from the flue gas by chemical reactions with an aqueous alkaline solvent, typically an amine. In the desorber, the absorbed $CO_2$ is stripped from the solvent at an elevated temperature with the heat supplied by the reboiler. The regenerated solvent from the desorber is sent back to the absorber after heat exchange with the $CO_2$-laden solvent from the absorber. The product stream from the desorber, comprising mostly $CO_2$ and water vapor, is sent for dehydration and $CO_2$ compression.

Total energy consumption in $CO_2$ absorption processes mainly comprises the heat usage for $CO_2$ desorption (i.e., solvent regeneration) and the work required for $CO_2$ compression. $CO_2$ desorption involves three elements of heat usage (in terms of kJ/kg $CO_2$ captured): (1) reaction heat required for the endothermic reaction of $CO_2$ desorption, (2) sensible heat consumed to heat up the $CO_2$-laden solution (after heat exchange in a cross-heat exchanger) to the regeneration temperature, and (3) stripping heat associated with water evaporation (proportional to the partial pressure ratio of $CO_2$ to water vapor in the product gas stream from the desorber). Superheated steam which is withdrawn from the power plant steam cycle or other steam generation facilities is generally used as a heat source in the reboiler. In addition, compression work is required to compress $CO_2$ from the desorption pressure (e.g., 20-30 psia in the benchmark MEA process) to the required high pressure (e.g., ~2,000 psia used for $CO_2$ geological sequestration).

Figure 2:
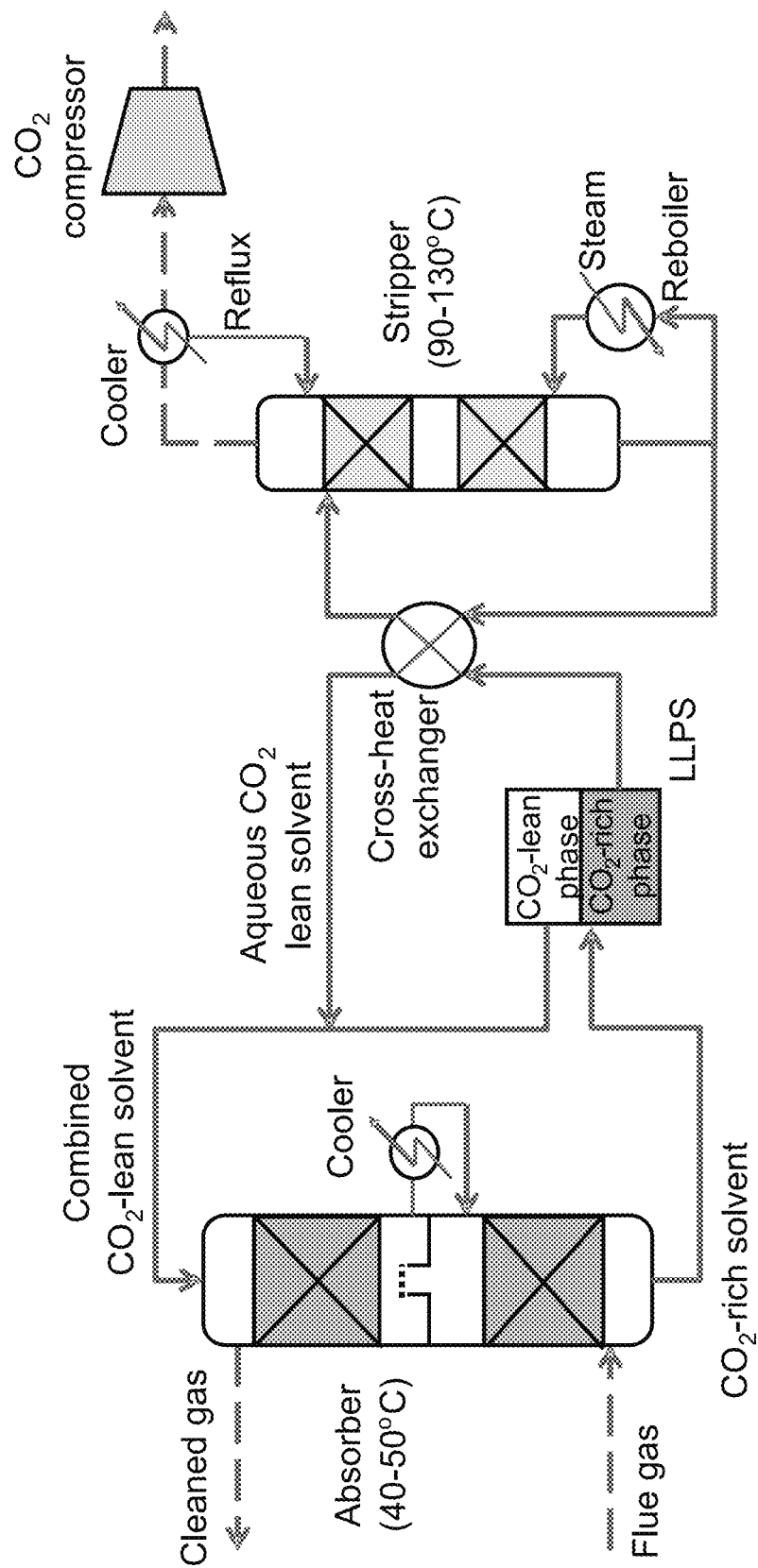
FIG. 2. Schematic diagram of biphasic $CO_2$ absorption processes for post-combustion $CO_2$ capture.

Biphasic solvent-based absorption processes have been investigated in recent years as an advanced PCC technology against the conventional monophasic absorption processes. FIG. 2 shows a schematic diagram of the commonly reported biphasic absorption processes. Compared with the conventional monophasic absorption processes, the biphasic processes have two major features: (1) the solvent undergoes a phase transition to form dual liquid phases upon the loading of $CO_2$ or a change of temperature; and (2) the formed two liquid phases are separated in a downstream phase separation unit, and only the resultant $CO_2$-rich phase solvent is fed into the desorber for regeneration.

Such biphasic absorption processes can reduce the heat use for solvent regeneration.

Because only the $CO_2$-rich phase is used for solvent regeneration, the mass of the solvent required to be regenerated decreases. Consequently, the heat required to heat the solvent (sensible heat) is reduced. Therefore, the biphasic process has potential in reducing the energy use for $CO_2$ capture compared with the benchmark MEA process.

During the absorption process, upon $CO_2$ loading, the biphasic solvent encounters a phase transition and forms dual liquid phases. After each stage of absorption, the $CO_2$-rich phase formed is partially separated from the solvent. The remaining solvent is cooled to the required temperature (30 to 50° C.) before entering the next stage of absorption. At the last stage, the solvent exiting the absorber is sent to an LLPS tank, where the $CO_2$-rich phase is pumped out and combined with the $CO_2$-rich streams from other stages of LLPS for $CO_2$ desorption. The $CO_2$-lean phase stream is mixed with the regenerated solvent from the stripper before recirculation to the absorber.

A portion of the $CO_2$-rich phase solvent is directly fed to the top of the stripper without heat exchange or slightly heated to be close to the temperature at the top of the stripper (i.e., cold rich solvent to the stripper). This cold rich solvent is further heated in the upper part of the stripper by the condensation of stripping steam. The other portion of the rich phase solvent is heated in a cross-heat exchanger with the hot regenerated solution obtained from the stripper and is then fed into the middle part of the stripper (i.e., hot rich solvent to the stripper). The stripper operates at a reboiler temperature of 120-150° C. and pressure of 1.5-6 bar. The $CO_2$ product stream from the stripper is cooled to remove water vapor and then compressed to a sequestration- or utilization-ready pressure. Depending on added operating complexity and equipment costs, the option exists to send the hot rich solvent to a flash unit to flash off a portion of $CO_2$ before it enters the stripper in order to obtain a $CO_2$ stream at a higher pressure than the stripper.

Figure 5:
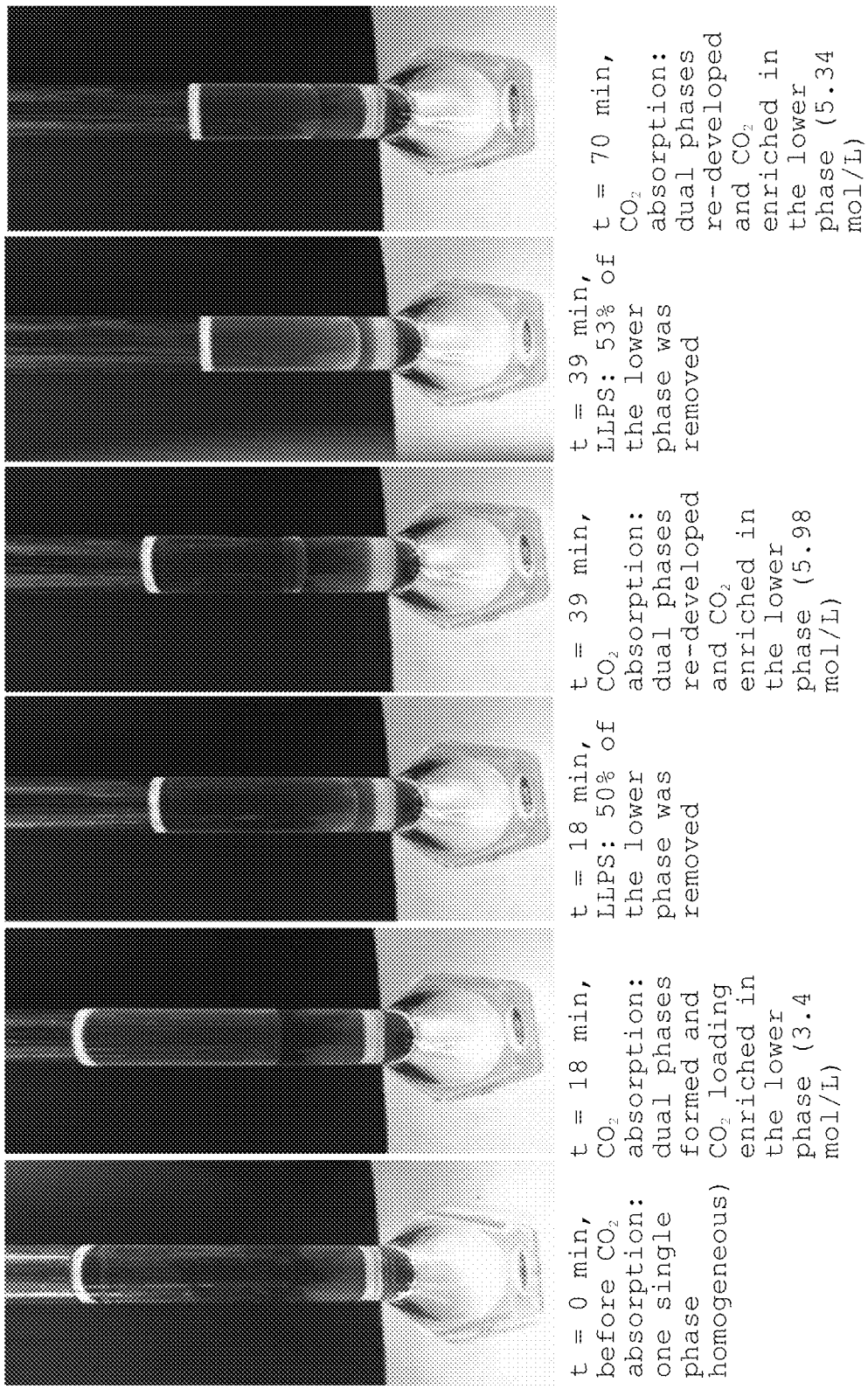
FIG. 5. Multiple stages of phase transition and separation during $CO_2$ absorption into the DETA+BDMAEE+DMI+$H_2O$ solvent blend as an example (the experiment conducted with pure $CO_2$ gas and at atmospheric pressure and 40° C.).

The disclosed biphasic solvents are also able to continuously form or remain the dual phases with increasing volume of the rich phase with loading of the $CO_2$ after the formed $CO_2$-rich phase is partially or completely separated and removed over the course of $CO_2$ absorption. FIG. 5 shows photographs of an exemplary biphasic solvent over three phase separation stages within 70 min of $CO_2$ absorption in pure $CO_2$ gas at 40° C. and atmospheric pressure. This solvent is a blend of a 1.8 M polyamine A (diethylenetriamine (DETA)) and a 1.5 M amino ether B (bis[2-(N,N-dimethylamino)ethyl] ether (BDMAEE)) in a 2.4 M organic solvent C (1,3-dimethyl-2-imidazolidinone (DMI)) and water, abbreviated as DETA+BDMAEE+DMI+$H_2O$ solvent. It was observed that the absorbed $CO_2$ was highly concentrated in the $CO_2$-rich phase liquid during the multiple absorption and phase separation stages. Over the three phase separation stages, the total amount of $CO_2$-rich phase solvent accounted for 61% of the final solvent volume, and the $CO_2$ loading in the combined $CO_2$-rich phase reached 4.95 mol/L, which was >11 times greater than that in the $CO_2$-lean liquid phase.

Figure 6:
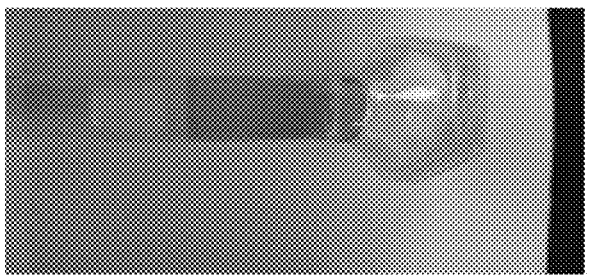
FIG. 6. Phase transition and separation achieved with one of the invented type of solvents (DETA+BDMAEE+DMI+$H_2O$) during $CO_2$ desorption (desorption at 80° C. in this illustration).
Figure 6:
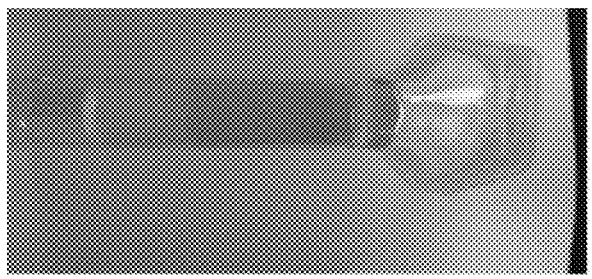
Figure 6:
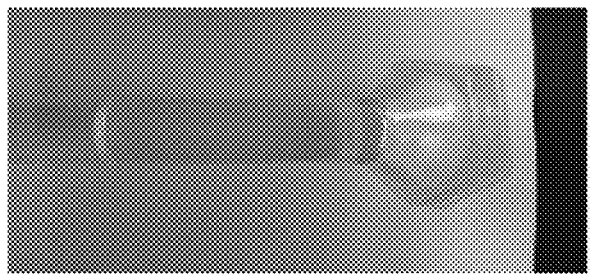

In most cases, the $CO_2$-rich phase used for thermal regeneration (separated from the $CO_2$-lean phase after the biphasic solvent is loaded with the $CO_2$) doesn't undergo a phase separation during $CO_2$ desorption. However, when it is necessary, by changing the composition of the biphasic solvent (e.g., by increasing the concentration of Component C), a phase transition can also occur for the $CO_2$-rich phase solvent during $CO_2$ desorption. For example, FIG. 6 displays photographs of dual phase transitions during the $CO_2$ desorption with the $CO_2$-rich phase derived from the DETA+BDMAEE+DMI+$H_2O$ biphasic solvent described above. In this illustration, the $CO_2$-rich phase solvent loaded with 4.52 mol/L $CO_2$ was heated at 80° C. The rich feed was a homogeneous solution and underwent a phase transition upon the stripping-off of $CO_2$. As shown in FIG. 6, when 18% of $CO_2$ in the rich phase solution was released, dual liquid phases were formed with the lower phase containing 5.23 mol/L $CO_2$ and the upper phase containing little $CO_2$ (0.17 mol/L). The volume of the lower phase accounted for about 70% of the total liquid volume when 18-23% of the $CO_2$ in the feed was desorbed. The formation of dual phases during $CO_2$ desorption is believed to be related to the difference of hydrophilicity between the molecular and ionic forms of compounds (Components A and B). When the $CO_2$ was desorbed, Components A and B were regenerated, and relatively more hydrophilic ionic species were converted to their molecular counterparts, which were more hydrophobic and could form a light oily phase even when there was no significant amount of organic solvent (Component C) present in the aqueous feed solution for the desorption.

For the developed biphasic solvents, the absorbed $CO_2$ can be concentrated in their rich phases (≥~95% of total $CO_2$ uptake in ≤~50 wt % of the original solution). Note that unlike the monophasic solvent processes (e.g., MEA), a phase separation step decouples the absorption and desorption processes, resulting in different $CO_2$ working capacities for $CO_2$ absorption and desorption. The absorption working capacities of the biphasic solvents are comparable to or up to 60% greater than that of 30% by weight MEA, and the $CO_2$ desorption working capacities are 2-4 times greater than that of 30% by weight MEA under comparable lean and rich $CO_2$ loadings (estimated at the conditions equivalent to about 0.1 and about 5 kPa of $CO_2$ equilibrium pressures, respectively, at 40° C.).

Figure 7:
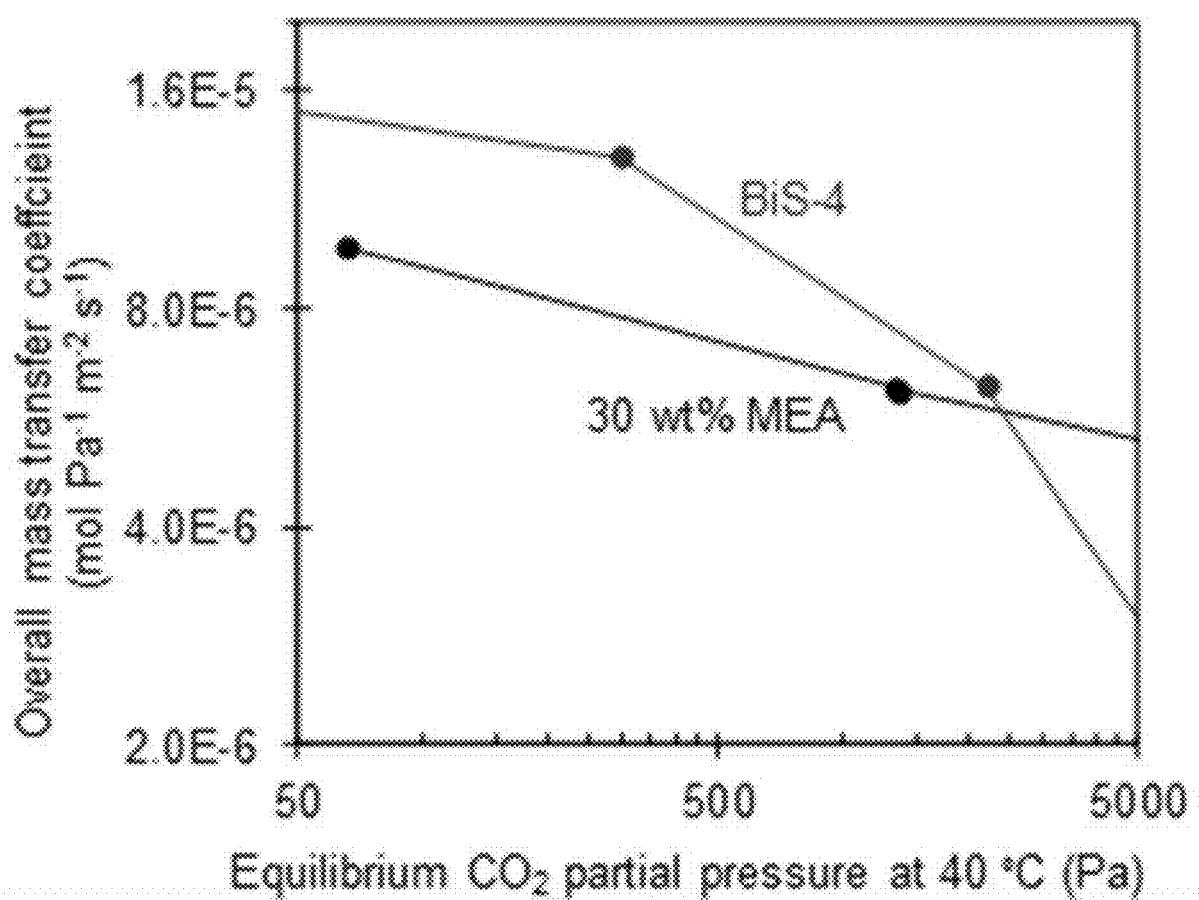
FIG. 7. Comparison of $CO_2$ absorption rates into BiS4 solvent as an example and 30% by weight MEA.

Solvent viscosity affects the operating performance and cost. For instance, the overall heat transfer coefficient decreases with increasing solvent viscosity following a power of –0.47 law. For most of the invented biphasic solvents, the viscosities of their lean phase samples are <9 cP and their rich phases after being saturated with $CO_2$ range between 20 and 100 cP (mostly below 50 cP) at 40° C. Rates of $CO_2$ absorption into the invented biphasic solvents were measured at 40° C. using a laboratory wetted wall column. As an example, FIG. 7 shows the absorption rate into the biphasic solvent, 2 M piperazine/2-methyl-piperazine+2 M 2-ethyl-4-methylimidazole+1.6 M tetraglyme aqueous blend (abbreviated as BiS4) as compared with the benchmark 30 wt % MEA solution. Although the viscosity of BiS4 is greater than that of 30 wt % MEA (~20 cP for the mixture of lean and rich phases vs. 3 cP for MEA), the rate into BiS4 is comparable to MEA. Fast absorption kinetics for the invented biphasic solvents can be attributable to the introductions of Component A as a rate promoter and organic Component C that enhances $CO_2$ physical solubility.

Figure 8:
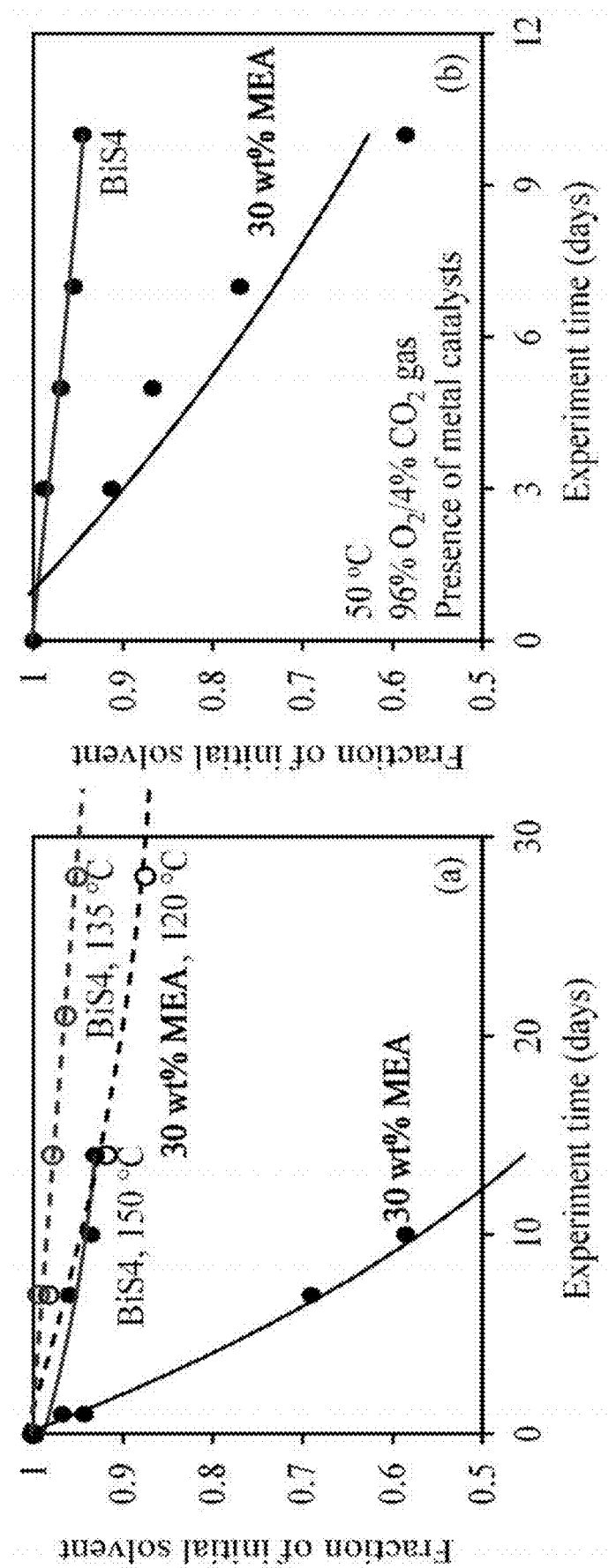
FIG. 8. Comparisons of (a) thermal degradation at 120 to 150° C. and (b) oxidative degradation in 96% $O_2$ at 50° C. between one selected biphasic solvent (BiS4) and 30% by weight MEA.

Among the biphasic solvents described herein, some have demonstrated both extremely high thermal and oxidative stabilities. The thermal stability was assessed at rich $CO_2$ loadings at 120-150° C. The oxidative degradation was assessed by bubbling a 96% $O_2$-4% $CO_2$ gas at 50° C. in the presence of several metal catalysts. As an example, FIG. 8 displays the stability of BiS4 solvent. It was observed that this solvent was highly stable: after 14 days at 150° C., only ~5% of the solvent mass (weight-averaged over all the solvent components) was lost compared with a ~50% solvent loss observed for 30% by weight MEA at the same temperature; the solvent was even more thermally stable at 135° C. than was MEA at 120° C. In the presence of 96% $O_2$, ~95% of the solvent (weight-averaged over all the solvent components) remained after 10 days at 50° C., significantly more stable than MEA, which retained only 59% of its initial amount.

Figure 12:
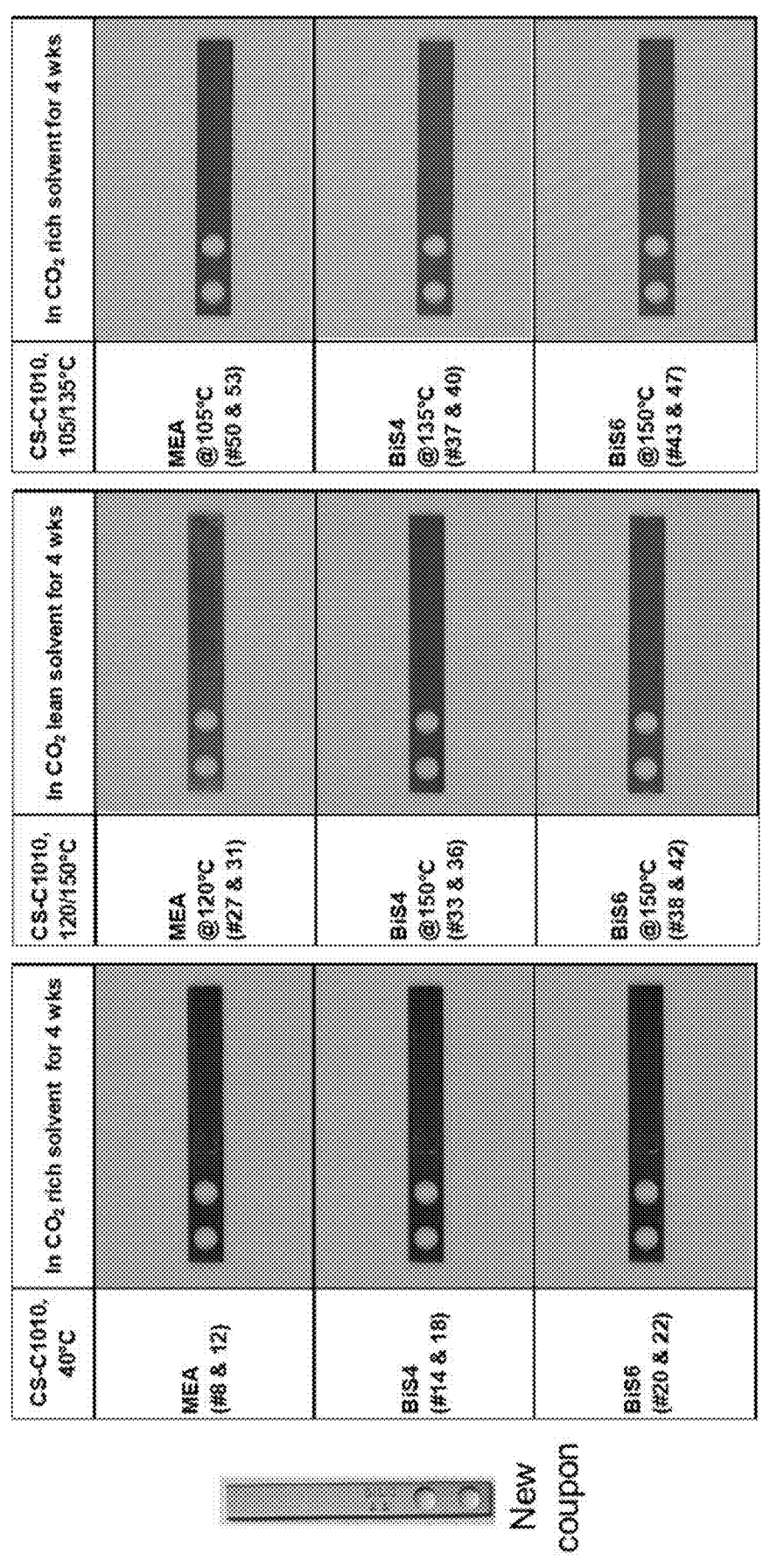
Figure 13:
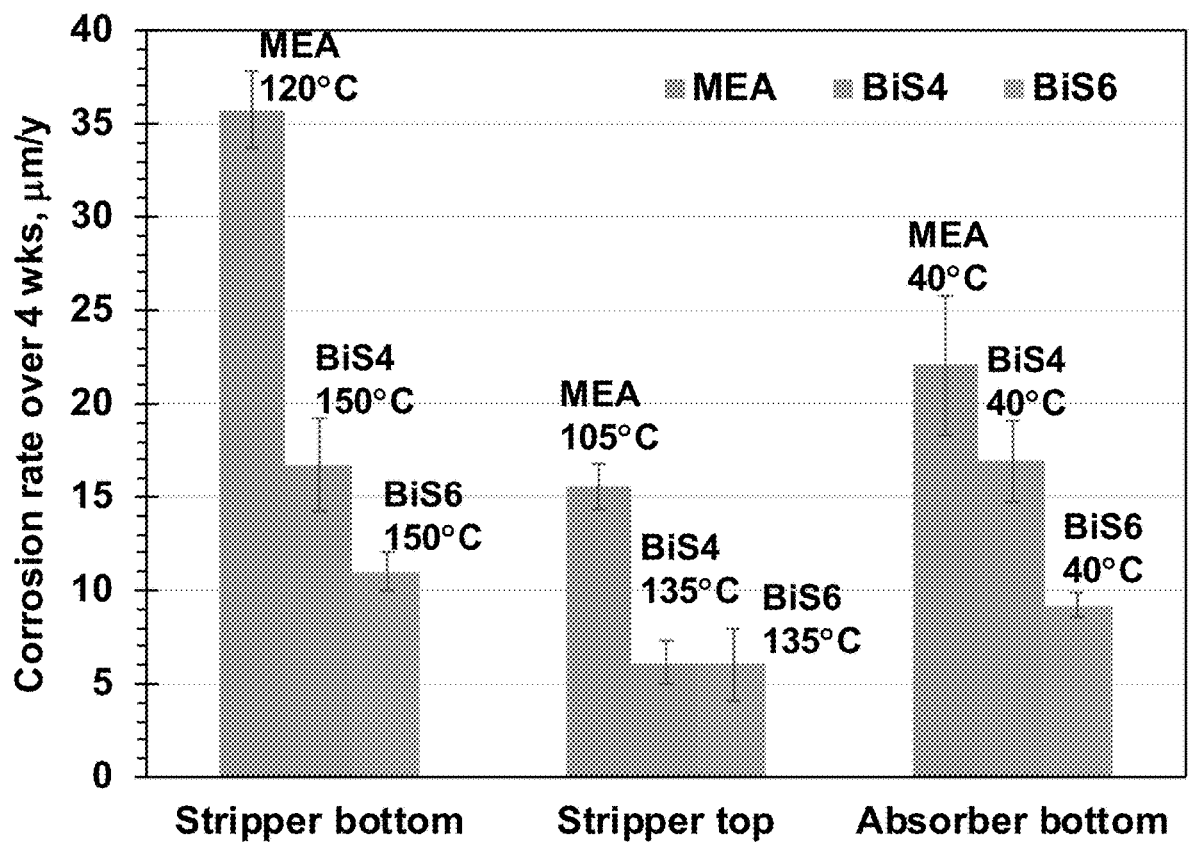
FIG. 13. Corrosion rates of carbon steel C1010 (CS-C1010) in 4 weeks. Corrosion rates of CS-C1010 were in the order of BiS6<BiS4<MEA. BiS6 and BiS4 were 2-3 times less corrosive than MEA.
Figure 14:
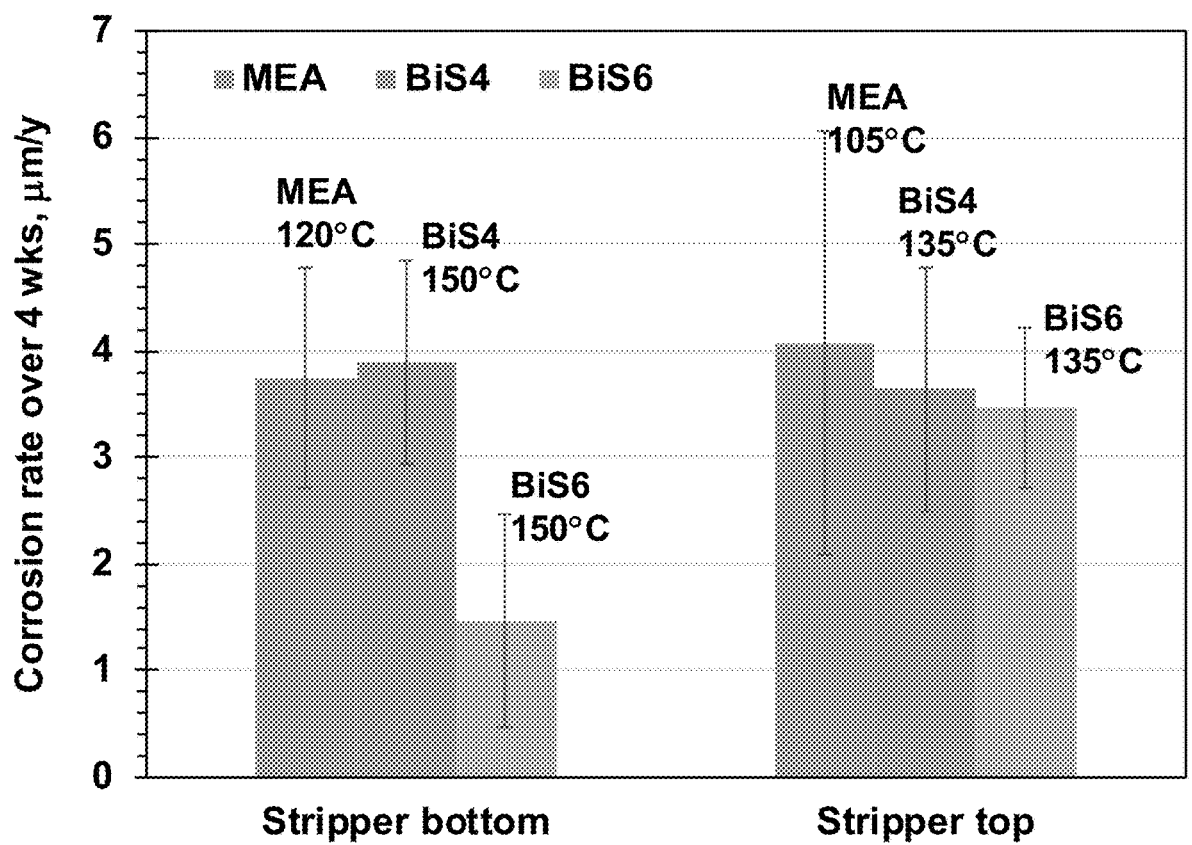
FIG. 14. Corrosion rates of stainless steel 316L (SS-316L) in 4 weeks. Corrosion rates of SS-316L (1.5-4 µm/y) were much lower than CS-C1010. No appreciable difference was observed in corrosion rate towards SS-316L coupons for BiS4, BiS6, and MEA under desorption conditions.

The impact of solvent corrosion on the carbon capture equipment was also assessed. Two steel coupons were tested to simulate equipment materials: carbon steel C1010 (CS-C1010) and stainless steel 316L (SS-316L). A weight-loss technique was applied to determine the corrosion rate of steel in the solvent. The method was based on the weight loss of the strip coupon before and after exposure to solvent corrosion. Coupons were immersed in solvents sealed in ½" outer diameter, 4.0" long stainless-steel tubes. The tubes were kept in incubators at required temperatures. After either a 2- or 4-week exposure, the coupons were weighed to calculate weight losses after cleanup including low-pressure glass bead blasting according to ASTM standard G1. FIG. 12 displays CS-C1010 coupons (before glass bead blasting cleaning) in MEA slightly darker than those in BiS4 and BiS6 biphasic solvents under the comparable test conditions. No visible etching and pitting were observed in all tests. As shown in FIG. 13, the corrosion rates of CS-C1010 were in the order of BiS6<BiS4<MEA, and the biphasic solvents BiS6 and BiS4 were 2-3 times less corrosive than MEA. FIG. 14 reveals that the corrosion rates of SS-316L (1.5-4 µm/y) were much lower than CS-C1010, and no appreciable difference was observed in corrosion rate towards SS-316L coupons for BiS4, BiS6, and MEA under the desorption conditions.

Approaches of Using the Disclosed Biphasic Solvents

Figure 9:
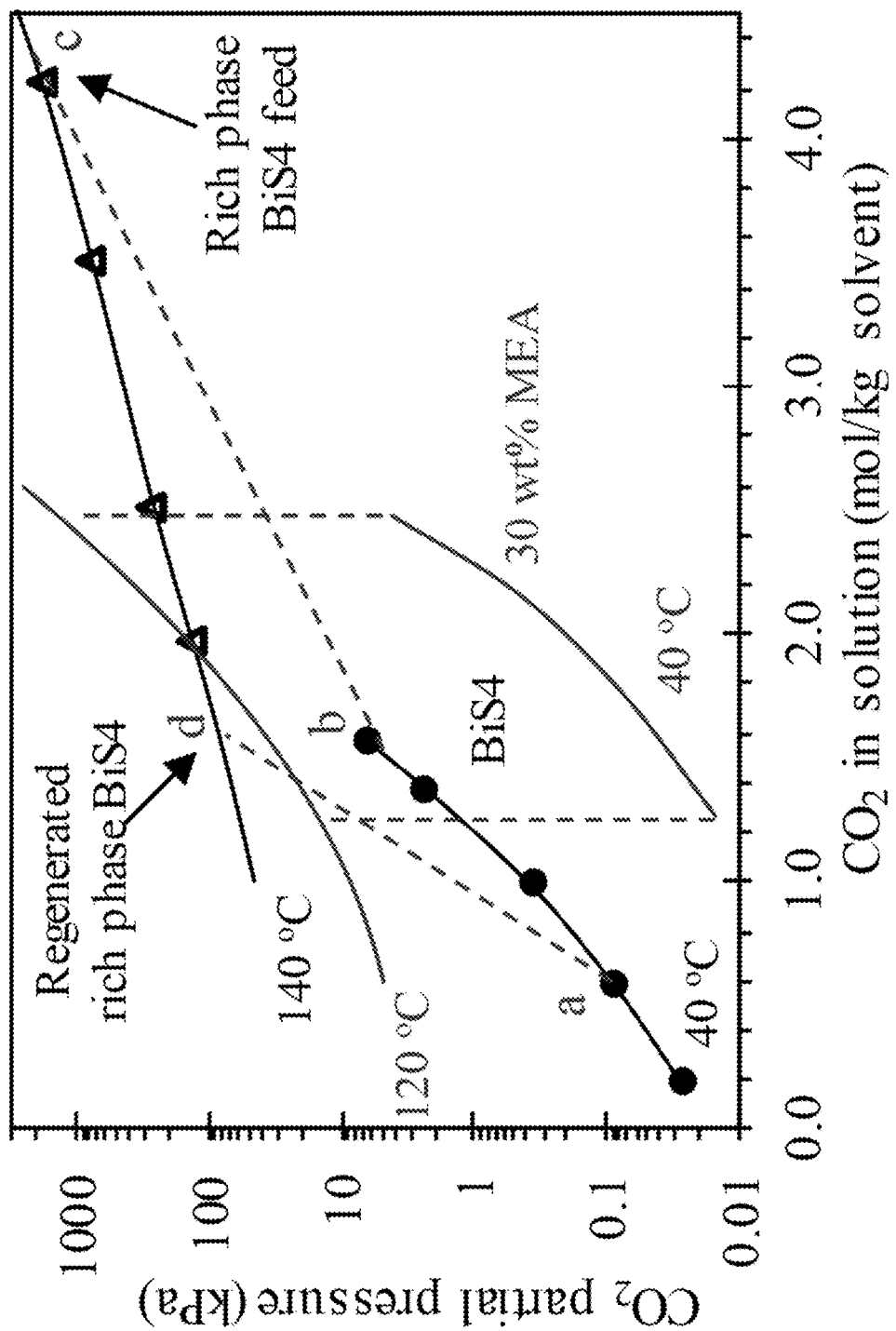
FIG. 9. Vapor-liquid equilibrium data for solvent BiS4 and 30% by weight MEA.

Process Variation 1:

One process approach using the disclosed biphasic solvents is described before as shown in FIG. 3. The vapor liquid equilibrium (VLE) data for solvent BiS4 under the typical absorption and desorption temperatures shown in FIG. 9 is used to illustrate the operation of the process approach. For comparison, the figure also shows published data for 30% by weight MEA.

The absorption step is illustrated by the VLE curve at 40° C. (Points a to b), assuming a 90% $CO_2$ removal rate (i.e., $CO_2$ pressure is reduced from 13 to 1.3 kPa for the typical post-combustion application) and the required mass transfer driving forces corresponding to the total $CO_2$ rich and lean loading equivalent to the equilibrium $CO_2$ pressures [$P_{CO2}$*] of 5 and 0.1 kPa, respectively. Under the comparable condition, the working capacity of BiS4 is similar to that of 30% by weight MEA (red curve at 40° C.).

Note that one stage of phase separation is considered in this example for illustrative purposes. After the $CO_2$ absorption, the $CO_2$-rich phase solvent is separated from the dual-phase mixture in a phase separator. Because of the phase separation, the $CO_2$ loading in the rich solvent increases to 4.2 mol of $CO_2$/kg of rich phase solvent (Point c in FIG. 9) from only 1.5 mol of $CO_2$/kg of solvent mixture (Point b).

The separated rich solvent is used as a feed for $CO_2$ desorption and solvent regeneration. After the rich phase solvent is regenerated, its $CO_2$ loading decreases to ~1.6 mol of $CO_2$/kg of rich phase solvent (Point d), which, after mixing with the $CO_2$-lean phase solvent, returns to the top of the absorber (Point a). Thus, the $CO_2$ working capacity during the $CO_2$ desorption step is estimated at 2.6 mol of $CO_2$/kg of solvent. In comparison, the $CO_2$ working capacity in the stripping process with 30% by weight MEA is typically estimated at 1.3 mol of $CO_2$/kg of solvent. Accordingly, the mass flow rate of the rich phase solvent to the BiCAP stripper can be only half of that of the MEA stripper, suggesting the desorption equipment with the invented solvent could be significantly smaller in size. In addition, the specific heat capacity of the rich phase solvent is <80% of that of 30% by weight MEA. Because of these two benefits, the total sensible heat use in this example is ~2.5 times lower than that of the MEA process.

The stripping configuration shown in FIG. 3 was simulated for solvent BiS4 with a rigorous rate-based model developed by the inventors. In this example, 30% of rich phase solvent was taken as a cold rich feed to the top of the stripper and the $CO_2$ stripping operated at a reboiler temperature of 140° C. and a pressure of 4.1 bar, with a $CO_2$ loading of 1.6 mol/kg of the regenerated solvent (a flash unit was not adopted here for simplicity of analysis). Because a cold rich solvent feed was introduced to the stripper top to recover the stripping heat by condensing more water vapor, a low water vapor-to-$CO_2$ ratio (~1:10) at 70-80° C. was achieved in the gas stream exiting the stripper. In conjunction with the benefit from the reduced mass of rich solvent for regeneration, the reboiler heat duty was reduced to 2.1 GJ/tonne of $CO_2$, which is much lower than that of 30% by weight MEA (3.6 GJ/tonne of $CO_2$). In addition, the higher operating pressure of the BiCAP stripper compared with the typical MEA stripper (~1.6 bar) can further reduce the work requirement for $CO_2$ compression.

This stripper configuration does not significantly increase the process complexity compared with the conventional simple stripper configuration. To allow the cold rich solvent to recover the heat from the stripping steam condensation, more stripper packing may be needed. On the other hand, because of the higher stripping temperature, $CO_2$ desorption is faster than for the MEA process. As a net effect, the packing height of the BiCAP stripper was estimated as comparable to that for MEA. However, because of the reduced mass of solvent for regeneration and increased stripping pressure, the diameter of the BiCAP stripper in this example was predicted to be ~50% smaller than for the MEA process.

Figure 10:
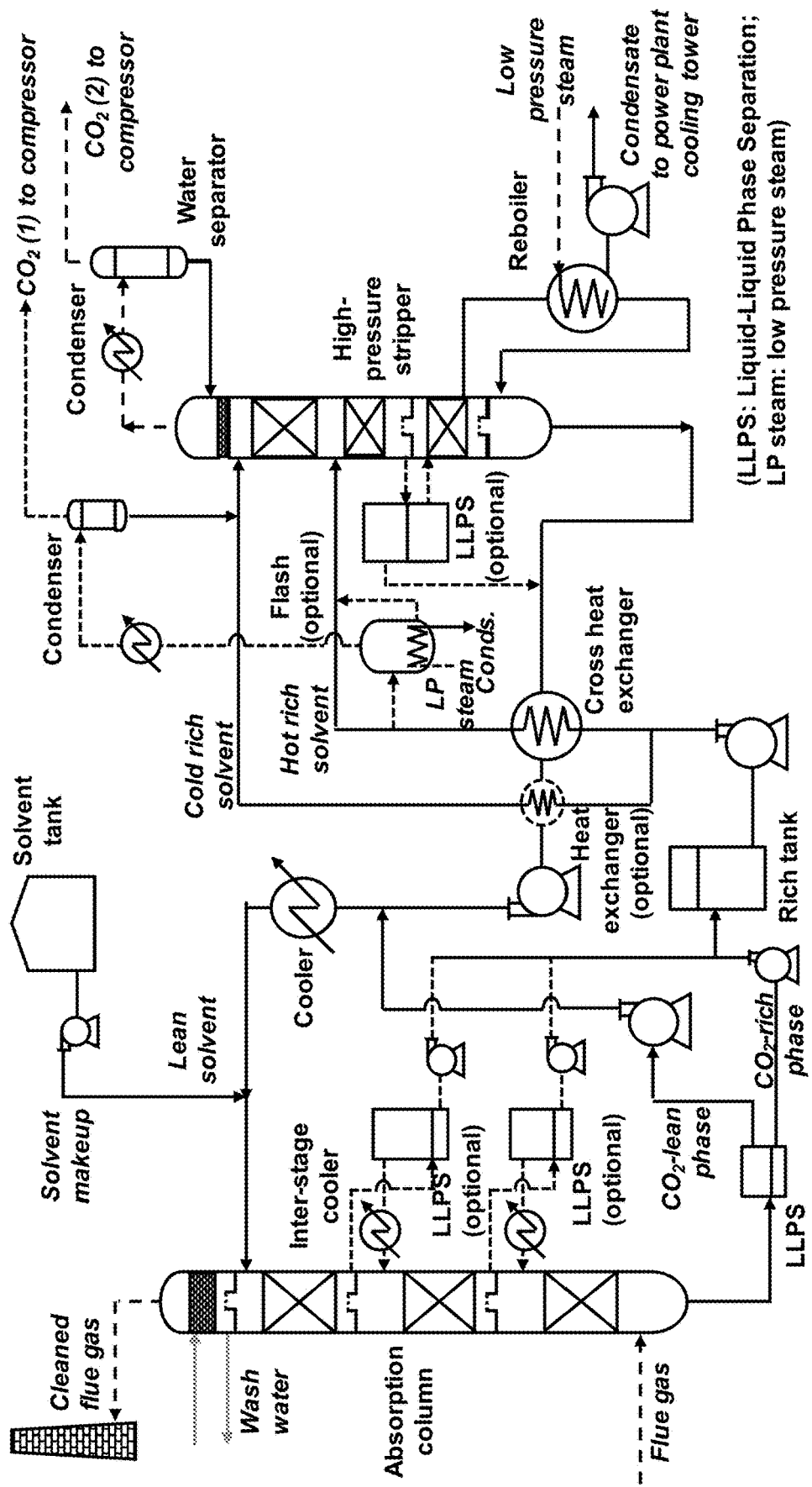
FIG. 10. Schematic diagram of the biphasic $CO_2$ absorption process (optional with multiple stages of liquid-liquid phase separation [LLPS] during $CO_2$ desorption). Two stages of LLPS during $CO_2$ desorption are shown in this illustration.

Process Variation 2:

Another process approach using the disclosed biphasic solvents incorporates a liquid-liquid phase separation operation in the $CO_2$ desorption (FIG. 10). As mentioned before, when necessary, the compositions of the developed biphasic solvents can be tuned to allow their $CO_2$-rich phases to undergo a phase transition and form two liquid phases, with the $CO_2$ lean in one phase and rich in the other, during the $CO_2$ desorption. As illustrated in FIG. 10, assuming a one-stage LLPS, the partially regenerated solvent flows out of the middle-packed bed, and only the $CO_2$-rich phase is sent to the lower bed for further solvent regeneration. The $CO_2$-lean liquid from the LLPS is combined to the regenerated solvent exiting the bottom of the stripper, and the mixture solvent is then cooled down in the cross-heat exchanger and recycled to the absorber. Note that one LLPS unit is illustrated in the desorption process in FIG. 10; however, two or more stages of LLPS units may be used, if necessary.

The incorporation of LLPS in the $CO_2$ desorption process has potential advantages of further reducing the energy use and desorption equipment footprint. The LLPS operation is performed to separate and remove the $CO_2$-lean phase liquid from the $CO_2$-rich phase liquid formed during the $CO_2$ desorption. As a result, a high level of $CO_2$ loading can be maintained over the course of $CO_2$ desorption, which allows the desorption operating at a high pressure. In addition, because a portion of the solvent (i.e., lean phase) is removed via the LLPS operation, the mass of the remaining solvent to the next stage of the desorber is reduced, potentially reducing the overall size of the desorber.

Figure 11:
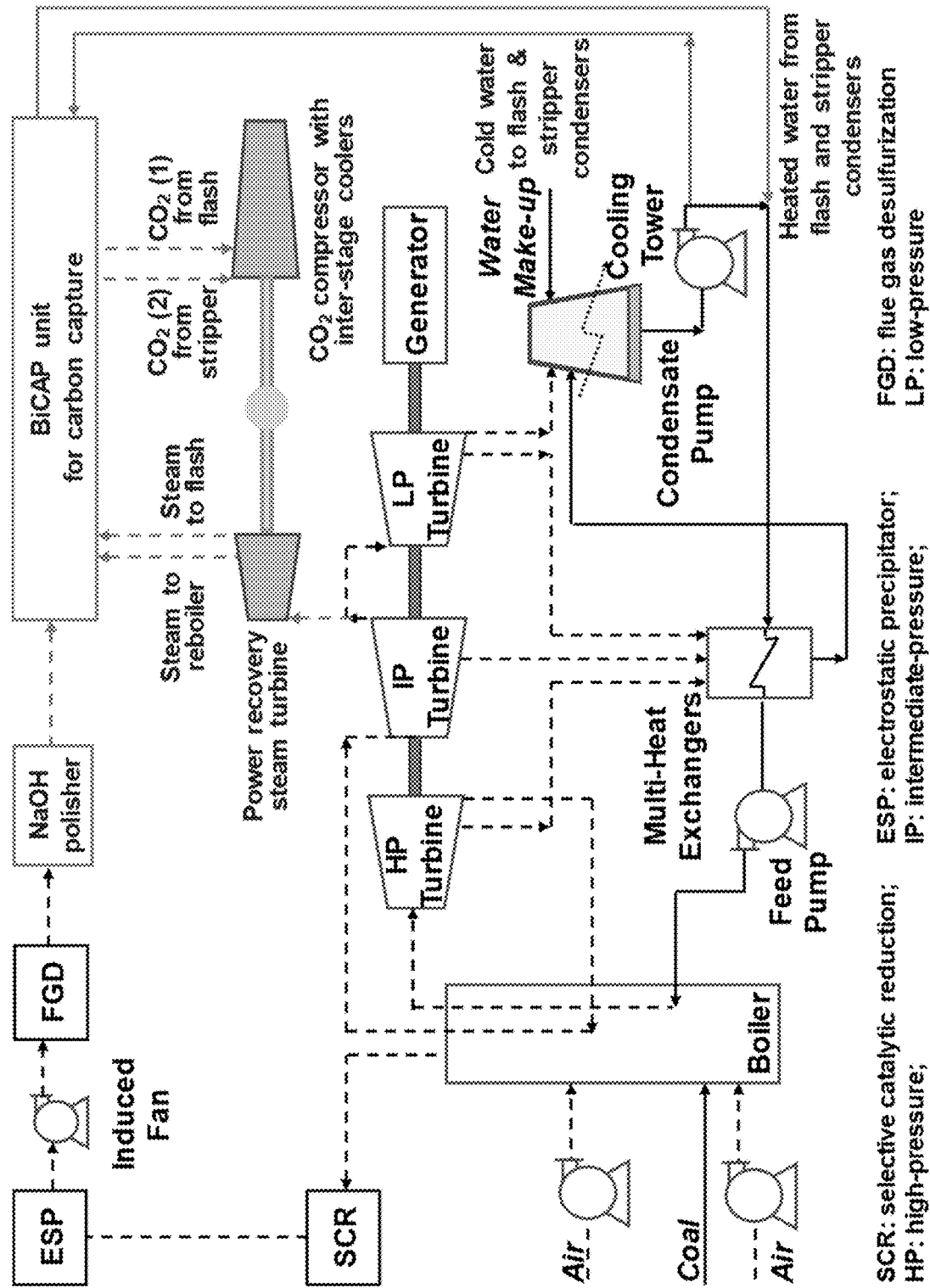
FIG. 11. Diagram showing integration of the BiCAP technology in a coal-fired power plant. See FIG. 10 for inset.

Integration with Industrial $CO_2$ Emission Sources:

The presently disclosed technology can be used to capture $CO_2$ from different fuel combustion and process sources (e.g., power plants, industrial boilers and kilns, and process exhaust gases containing $CO_2$). FIG. 11 illustrates the integration of the BiCAP into a pulverized coal (PC)-fired power plant. Before entering the capture system, the flue gas from the flue gas desulfurization (FGD) unit of the power plant is purified in an alkali (e.g., NaOH) polishing device to reduce $SO_x$ to <10 ppm and cool the flue gas to ≤40° C. The flue gas then enters the absorber and leaves as a clean gas. The steam used in the BiCAP flash (optional) and stripper is extracted at the exit of the power plant's intermediate-pressure turbine. This steam is directed to a power recovery steam turbine, and the resulting streams of reduced-pressure steam are introduced into the stripper reboiler and the flash, respectively, corresponding to their required operating temperatures. A portion of the power plant feed water is used as a cooling medium in the stripper condenser to recover the heat contained in the hot $CO_2$ product streams.

The rigorous rate-based model was used to simulate the BiCAP technology, with solvent BiS4 and the configuration shown in FIG. 3 as an example, integrated with a 550 MWe (net) supercritical PC-fired power plant according to the operating conditions described above and the USDOE Case 12 design basis.

Mass and energy balance information was obtained by the process simulation. Table 1 summarizes the results of energy use. The total electricity loss attributable to steam extraction to the reboiler accounts for 71 MWe, which is lower than the 139 MWe in the MEA process (Base Case 12). Because of the high-pressure $CO_2$ stream exiting the stripper (4.1 bar), the BiCAP also reduces the $CO_2$ compression work (32 MWe) by ~30% compared with the MEA process (45 MWe). Overall, the total parasitic power loss in the BiCAP is ~43% lower than that in USDOE Case 12. This can be translated to an energy use intensity of 0.24 kWh/kg of $CO_2$ captured (including $CO_2$ compression) for the BiCAP compared with 0.37 kWh/kg for the MEA process and 0.29 kWh/kg for the Cansolv process. Note that this BiCAP case is an example for the analysis and is not an optimized one. With the process optimized (e.g., percentage and temperature of cold rich feed and location of the hot rich feed in the stripper), the energy use is expected to be reduced to ≤0.22 kWh/kg of $CO_2$ captured.

TABLE 1

Estimation of derating and parasitic power use for $CO_2$ capture in a 550 MWe (net) power plant.

| | BiCAP | USDOE Case 12 (MEA) | USDOE Case B12B (Cansolv) |
|---|---|---|---|
| Net Generating Capacity, MWe | 550 | 550 | 550 |
| Gross Generating Capacity, MWe | 700 | 802 | 728 |
| Amount of $CO_2$ captured, tonne/hr | 478 | 548 | 480 |
| Total Steam Derate, MWe | 71.1 | 139 | 86 |
| Reboiler/Flash Heat Duty, MWth | 278 | 542 | 331 |
| Thermal to Electric Energy, % | 25.6 | 25.6 | 25.8 |
| Direct Electrical Derate, MWe | 44.8 | 65.5 | 51.7 |
| Compression Duty, MWe | 31.5 | 44.9 | 35.7 |
| Other (Pumps, Fans, etc.), MWe | 13.3 | 20.6 | 16.0 |
| Total Derate for $CO_2$ Capture, MWe | 116 | 204 | 137 |
| Total parasitic use for entire plant, MWe | 150 | 252 | 178 |

Preliminary equipment sizing and economic estimates were also conducted based on the mass and energy balance information described above. The BiCAP can reduce the total plant cost and all the operating costs (fixed, variable, and fuel costs). These benefits are related in part to the improved energy performance described above. Additional benefits are accrued from the reduced costs associated with major equipment, including the absorber, stripper, and compressor.

Lab-scale absorption column experiments revealed that the biphasic solvents invented could have faster absorption rates than the benchmark 30% by weight MEA. For example, solvent BiS4 exhibited ~1.5 times higher absorption rates because of the faster kinetics and use of a larger liquid/gas ratio (L/G) compared with that for MEA. This yielded an absorber size ~12% smaller than that required for USDOE Case 12 (MEA).

The $CO_2$ product stream from the BiCAP has a higher pressure than that from the MEA. For example, the $CO_2$ product stream was generated at 4.1 bar from the stripper of the BiCAP with solvent BiS4. The higher suction pressure and reduced $CO_2$ flow rate (resulting from the higher energy efficiency) significantly reduced the compression work requirement of the BiCAP compared with USDOE Case 12.

The stripping column size for the BiCAP is smaller because of the reduced mass of rich phase solvent used for $CO_2$ desorption and the higher desorption pressure attained compared with USDOE Case 12.

It should be noted that the adverse effect of higher viscosity of the rich phase solvent on the size of the cross-heat exchanger as compared with the MEA needs be considered in the economic evaluation. In addition, the LLPS equipment incurs additional costs unique to the BiCAP. Overall, the preliminary economics indicates that compared with USDOE Case 12 (MEA), the total power plant costs installed with the BiCAP are reduced by 20-30% and the operating costs are reduced by 15-25%. The BiCAP resulted in a 30-45% reduction in the cost of $CO_2$ captured over the baseline values of USDOE Case 12 (MEA).

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. General Components for Carbon Dioxide Capture

Component A is a compound which has at least one active primary or secondary amino group that reacts with carbon dioxide ($CO_2$) to consume $CO_2$, by forming a carbamate species. Note that in both reactions shown below, water is not a reactant. In either case, the proton generated can be accepted by any base species in the mixture. Examples of primary and secondary amines that are reactive with carbon dioxide are shown in Table 2.

$$R-NH_2 \text{ (i.e. a primary amine)} + CO_2 \rightarrow R-NHCOO^- + H^+$$

$$R^1R^2-NH \text{ (i.e. a secondary amine)} + CO_2 \rightarrow R^1R^2-NCOO^- + H^+$$

$$H^+ + Base \rightarrow BaseH^+$$

TABLE 2

Component A: Nucleophilic amines reactive with carbon dioxide.

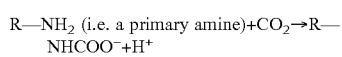

3-(Aminomethyl)pyridine

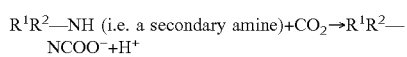

4-(2-Aminoethyl)morpholine

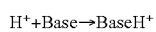

Hexylamine

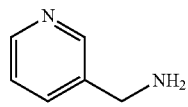

2-Piperidineethanol

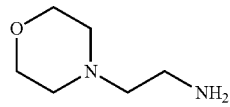

Piperazine

1-(2-Aminoethyl)piperazine

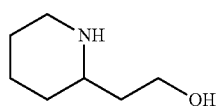

bis(2-aminoethyl) ether

TABLE 2-continued

Component A: Nucleophilic amines reactive with carbon dioxide.

Hexamethyleneimine

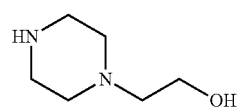

1-(2-Hydroxyethyl)piperazine

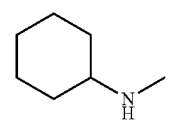

N-Methylcyclohexylamine

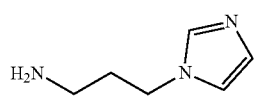

1-(3-aminopropyl)imidazole

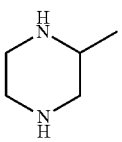

2-Methyl-piperazine

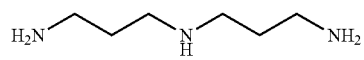

Bis(3-aminopropyl)amine

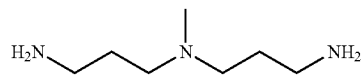

3,3'-diamino-N-methyldipropylamine

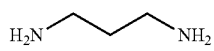

1,3-Diaminopropane

Component B is a compound that is an acceptor of protons, such as a nitrogen heterocycle, or a compound which has at least one tertiary or sterically hindered amino group. The protons are generated by dissolution reaction between $CO_2$ and $H_2O$, shown in the reaction mechanisms below. Examples of proton acceptors (e.g. basic nitrogen compounds) are shown in Table 3.

Base catalyzed dissolution reaction of $CO_2$:

$$R^1R^2R^3-N + H_2O + CO_2 \rightarrow HCO_3^- + R^1R^2R^3-NH^+$$

$$HCO_3^- \rightarrow H^+ + CO_3^{2-}$$

TABLE 3

Component B: Basic nitrogen compounds as proton acceptors (Brønsted bases).

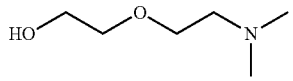

Dimethylaminoethoxyethanol

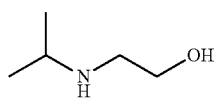

2-(isopropylamino)ethanol

Triethylenediamine

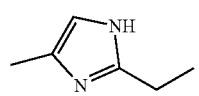

2-Ethyl-4-methylimidazole

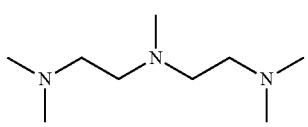

N,N,N',N'',N''-Pentamethyldiethylenetriamine

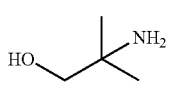

2-amino-2-methyl-1-propanol

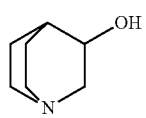

3-Quinuclidinol

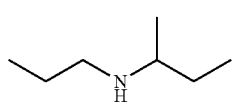

N-Propyl-sec-butylamine

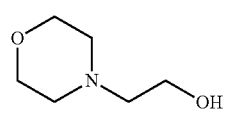

4-(2-Hydroxyethyl)morpholine

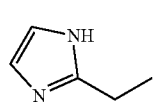

2-Ethylimidazole

TABLE 3-continued

Component B: Basic nitrogen compounds as proton acceptors (Brønsted bases).

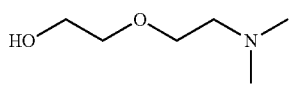

4-Hydroxy-1-methylpiperidine

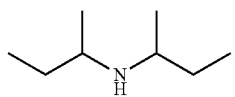

Di-sec-butylamine

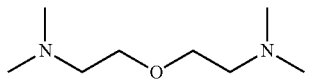

Bis[2-(N,N-dimethylamino)ethyl]ether

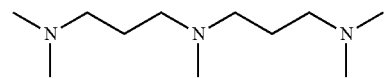

N,N,N',N'',N''-pentamethyl-dipropylenetriamine

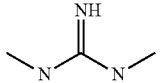

1,1,3,3-Tetramethylguanidine

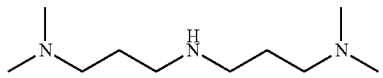

3,3'-iminobis(N,N-dimethylpropylamine)

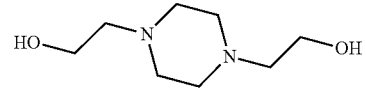 [SMILES: OCCN1CCN(CCO)CC1]

1,4-bis(2-hydroxyethyl)piperazine

Example 2. Composition of BiS4

A freshly prepared solution of BiS4 (containing no added amount of $CO_2$) comprises piperazine 8.5 wt %, 2-methylpiperazine 9.9 wt %, 2-ethyl-4-methylimidazole 21.6 wt %, tetraglyme 35.0 wt % and water 25.0 wt %. The fresh BiS4 solution was completely (100%) a homogeneous solution.

Example 3. Composition of BiS6

A freshly prepared solution of BiS6 (containing no added amount of $CO_2$) comprises piperazine 5 wt %, 2-methylpiperazine 10 wt %, 2-[2-(dimethylamino)ethoxy]ethanol 20 wt %, tetraglyme 40 wt % and water 25 wt %. The fresh BiS6 solution was completely (100%) a homogeneous solution.

Example 4. Composition of BiS2

A freshly prepared solution of BiS2 (containing no added amount of $CO_2$) comprises piperazine 11 wt %, 4-hydroxy- 1-methylpiperidine 29 wt %, tetraglyme 40 wt % and water 20 wt %. The fresh BiS2 solution was completely (100%) a homogeneous solution.

Example 5. Composition of BiS1

A freshly prepared solution of BiS1 (containing no added amount of $CO_2$) comprises bis-(2-aminoethyl)ether 26 wt %, 2-[2-(dimethylamino)ethoxy]ethanol 24 wt %, tetraglyme 30 wt % and water 20 wt %. The fresh BiS1 solution was completely (100%) a homogeneous solution.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An aqueous composition comprising:
   a) at least two nucleophilic compounds, wherein the nucleophilic compounds comprise a sterically unhindered primary amine moiety, a sterically unhindered secondary amine moiety, or a combination thereof;
   b) at least one Brønsted base, wherein the Brønsted base comprises a basic nitrogen moiety and the Brønsted base does not comprise a sterically unhindered primary amine moiety and a sterically unhindered secondary amine moiety;
   c) about 30% to about 50% by weight of a water-soluble organic solvent, wherein the organic solvent is a glyme; and
   d) about 20% to about 40% by weight of water;
   wherein the composition is a homogeneous mixture within the temperature range of 20° C. to 80° C.

2. The composition of claim 1 wherein the water-soluble organic solvent is tetraglyme, the Brønsted base is 2-ethyl-4-methylimidazole or 2-[2-(dimethylamino)ethoxy]ethanol, and the at least two nucleophilic compounds comprise piperazine and 2-methylpiperazine.

3. The composition of claim 1 wherein
   the combination of the nucleophilic compounds, the Brønsted base, the organic solvent, and the water components of the composition are completely miscible within the temperature range of 20° C. to 80° C.;
   the boiling points of the nucleophilic compounds, Brønsted base, and organic solvent are each at least 140° C.; and
   the vapor pressures of the nucleophilic compounds, Brønsted base, and organic solvent are each about 100 Pa or below at about 20° C.

4. The composition of claim 1 wherein the composition comprises about 10% to about 35% by weight of the Brønsted base, and about 10% to about 35% by weight of the nucleophilic compounds.

5. The composition of claim 4 wherein the composition comprises 15 wt. % to 25 wt. % of the Brønsted base.

6. The composition of claim 4 wherein the composition comprises 15 wt. % to 25 wt. % of the nucleophilic compounds.

7. The composition of claim 1 wherein the Brønsted base comprises an imidazole, a piperazine, a morpholine, a piperidine, a non-alcoholic tertiary amine, a non-alcoholic sterically hindered amine, or a combination thereof; and the molecular weight of the Brønsted base is about 60 daltons to about 250 daltons.

8. The composition of claim 1 wherein the Brønsted base is 2-ethylimidazole, 2-ethyl-4-methylimidazole, 1,4-bis(2-hydroxyethyl)piperazine, 4-(2-hydroxyethyl)morpholine, 4-hydroxy-1-methylpiperidine, bis[2-(N,N-dimethylamino)ethyl] ether, N,N,N',N'',N''-pentamethyldiethylenetriamine, N,N,N',N'',N''-pentamethyldipropylenetriamine, triethylenediamine, 3,3'-iminobis(N,N-dimethylpropylamine), di-sec-butylamine, N-propyl-sec-butylamine, 2-[2-(dimethylamino)ethoxy]ethanol, or a combination thereof.

9. The composition of claim 1 wherein the first nucleophilic compound of the at least two nucleophilic compounds is a piperazine, a morpholine, an amino ether, a non-alcoholic polyamine, a non-alcoholic monoamine, or a combination thereof.

10. The composition of claim 1 wherein the second nucleophilic compound of the at least two nucleophilic compounds is 2 methyl-piperazine, 1-(2-hydroxyethyl)piperazine, 1-(2-aminoethyl)piperazine, 4-(2-aminoethyl)morpholine, bis(2-aminoethyl) ether, bis(3-aminopropyl)amine, 1,3-diaminopropane, 3,3'-diamino-N-methyldipropylamine, 3-(aminomethyl)pyridine, 1-(3-aminopropyl)imidazole, hexamethyleneimine, N-methylcyclohexylamine, or a combination thereof.

11. The composition of claim 10 wherein the second nucleophilic compound is 2-methyl-piperazine.

12. The composition of claim 1 wherein the viscosity of the composition is 10 cP or less at 20° C.

13. The composition of claim 12 wherein the water-soluble organic solvent comprises triethylene glycol dimethyl ether (triglyme), tetraethylene glycol dimethyl ether (tetraglyme), or a combination thereof.

14. A method for capturing carbon dioxide comprising contacting carbon dioxide gas with an aqueous composition according to claim 1;
   wherein
   a) the at least two nucleophilic compounds and carbon dioxide gas form a carbamate moiety via the nitrogen atom of the sterically unhindered primary or sterically unhindered secondary amine moiety to provide carbamate compounds;
   b) the Brønsted base forms a conjugate acid wherein the dissolution of carbon dioxide gas is facilitated;
   c) the water in the aqueous composition becomes enriched with the carbamate compounds; and
   d) the aqueous composition partitions to form a biphasic composition that has a $CO_2$-rich phase and a $CO_2$-lean phase, wherein the rich phase comprises the highest % weight of water, the highest % weight of the carbamate compounds, and the highest % weight of the conjugate acid; and the lean phase comprises the highest % weight of the organic solvent;
   wherein carbon dioxide is thereby captured.

15. The method of claim 14 wherein the organic solvent comprises tetraglyme, the Brønsted base is 2-ethyl-4-methylimidazole, and the at least two nucleophilic compounds comprise piperazine and 2-methylpiperazine.

16. The method of claim 14 further comprising heating the $CO_2$-rich phase at about 100° C. to about 160° C. to release captured carbon dioxide as molecular carbon dioxide; and optionally recovering recycled nucleophilic compounds and Brønsted bases;

wherein the amount of energy used to release molecular carbon dioxide at 100° C. to 160° C. is less compared to the release of molecular carbon dioxide from a monophasic composition comprising 30% by weight of monoethanolamine at 100° C. to 125° C.

17. A method of processing carbon dioxide comprising:
a) contacting carbon dioxide gas and the aqueous composition according to claim 1 in one or more absorption columns to form a biphasic composition comprising carbamate compounds, a $CO_2$-rich phase, and a $CO_2$-lean phase;
b) at least partially separating the $CO_2$-rich phase from the $CO_2$-lean phase in one or more liquid-liquid phase separation (LLPS) units, wherein the at least partially separated $CO_2$-rich phase is dispatched from the one or more LLPS units;
c) feeding the $CO_2$-rich phase to one or more thermal strippers and heating the $CO_2$-rich phase to a temperature that releases an amine compound and molecular carbon dioxide from the carbamate compound;

wherein
  i) the $CO_2$-rich phase is optionally preheated, wherein the preheated $CO_2$-rich phase is fed to the middle or lower portion of the one or more thermal strippers; or
  ii) the $CO_2$-rich phase is not preheated, wherein the not preheated $CO_2$-rich phase is fed to the top portion of the one or more thermal strippers;
d) returning the amine compound to the one or more absorption columns;
e) compressing the molecular carbon dioxide with one or more compressors into liquid carbon dioxide; and
f) optionally at least partially separating a second $CO_2$-lean phase is from a second $CO_2$-rich phase in a second LLPS unit and dispatching the at least partially separated second $CO_2$-lean phase from the second LLPS unit, wherein the one or more thermal strippers comprise the second LLPS unit;

wherein carbon dioxide is thereby processed from a gas to a liquid.

* * * * *